United States Patent
Garizi et al.

(10) Patent No.: US 9,210,931 B2
(45) Date of Patent: Dec. 15, 2015

(54) PESTICIDAL COMPOSITIONS AND PROCESSES RELATED THERETO

(71) Applicant: Dow AgroSciences LLC, Indianapolis, IN (US)

(72) Inventors: Negar Garizi, Westfield, IN (US); Maurice C. Yap, Zionsville, IN (US); Tony K. Trullinger, Westfield, IN (US); CaSandra L. McLeod, Indianapolis, IN (US); Paul Renee LePlae, Jr., Brownsburg, IN (US); Timothy C. Johnson, Indianapolis, IN (US); Ricky Hunter, Westfield, IN (US); John F. Daeuble, Sr., Carmel, IN (US); Ann M. Buysse, Carmel, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 14/747,170

(22) Filed: Jun. 23, 2015

(65) Prior Publication Data

US 2015/0289509 A1 Oct. 15, 2015

Related U.S. Application Data

(60) Continuation of application No. 14/158,274, filed on Jan. 17, 2014, which is a division of application No. 13/285,471, filed on Oct. 31, 2011, now Pat. No. 8,680,121.

(60) Provisional application No. 61/409,739, filed on Nov. 3, 2010.

(51) Int. Cl.

| | |
|---|---|
| *A01N 43/50* | (2006.01) |
| *A01N 63/04* | (2006.01) |
| *A01N 25/00* | (2006.01) |
| *A01N 63/00* | (2006.01) |
| *A01N 47/18* | (2006.01) |
| *C05G 3/02* | (2006.01) |
| *C07D 401/04* | (2006.01) |
| *C05C 3/00* | (2006.01) |

(52) U.S. Cl.
CPC ............... *A01N 43/50* (2013.01); *A01N 25/00* (2013.01); *A01N 47/18* (2013.01); *A01N 63/00* (2013.01); *A01N 63/04* (2013.01); *C05C 3/00* (2013.01); *C05G 3/02* (2013.01); *C07D 401/04* (2013.01)

(58) Field of Classification Search
CPC ....... A01N 43/50; A01N 63/04; A01N 25/00; A01N 63/00; A01N 47/18; C05G 3/02; C07D 401/04; C05C 3/00
See application file for complete search history.

(56) References Cited

U.S. PATENT DOCUMENTS

| | | |
|---|---|---|
| 7,192,906 B2 | 3/2007 | Hirohara et al. |
| 2004/0248958 A1 | 12/2004 | Holmwood et al. |
| 2008/0027046 A1 | 1/2008 | Annan et al. |
| 2009/0137524 A1 | 5/2009 | Billen et al. |
| 2010/0204164 A1 | 8/2010 | Crouse et al. |

FOREIGN PATENT DOCUMENTS

| | | |
|---|---|---|
| WO | WO/2011/058571 | 3/2012 |
| WO | WO/2012/061288 | 5/2012 |

*Primary Examiner* — Trevor Love
(74) *Attorney, Agent, or Firm* — Carl D. Corvin

(57) ABSTRACT

This document discloses molecules having the following formula (Formula One)

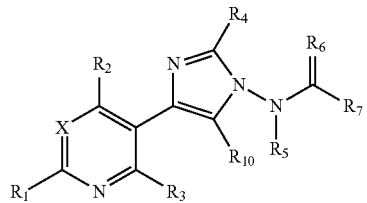

Formula One and processes related thereto.

48 Claims, No Drawings

PESTICIDAL COMPOSITIONS AND PROCESSES RELATED THERETO

CROSS REFERENCE TO RELATED APPLICATIONS

This Application is a continuation of U.S. patent application Ser. No. 14/158,274, which was filed on Jan. 17, 2014, which is a divisional of U.S. patent application Ser. No. 13/285,471, now U.S. Pat. No. 8,680,121, which was filed on Oct. 31, 2011, which claims the benefit of, and priority from, U.S. Provisional patent application Ser. No. 61/409,379, which was filed Nov. 3, 2010, the entire disclosures of these applications are hereby incorporated by reference.

FIELD OF THIS DISCLOSURE

This disclosure is related to the field of processes to produce molecules that are useful as pesticides (e.g., acaricides, insecticides, molluscicides, and nematicides), such molecules, and processes of using such molecules to control pests.

BACKGROUND

Pests cause millions of human deaths around the world each year. Furthermore, there are more than ten thousand species of pests that cause losses in agriculture. The worldwide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides.

Therefore, for many reasons, including the above reasons, a need exists for new pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, ($C_3$)alkyl which represents n-propyl and isopropyl), ($C_4$)alkyl which represents n-butyl, sec-butyl, isobutyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"($C_x$-$C_y$)" where the subscripts "x" and "y" are integers such as 1, 2, or 3, means the range of carbon atoms for a substituent—for example, ($C_1$-$C_4$)alkyl means methyl, ethyl, n-propyl, isopropyl, n-butyl, sec-butyl, isobutyl, and tert-butyl, each individually.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl. Additional examples include the following

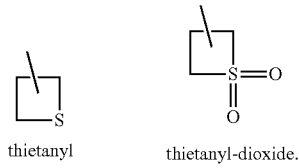

thietanyl   thietanyl-dioxide.

DETAILED DESCRIPTION

This document discloses molecules having the following formula ("Formula One"):

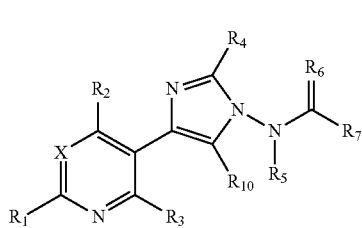

Formula One wherein
(a) X is N or CR8;
(b) R1 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
  wherein each said R1, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);
(c) R2 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
  wherein each said R2, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);
(d) R3 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
  wherein each said R3, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);
(e) R4 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
  wherein each said R4, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);
(f) R5 is H, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl)S(O)$_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_6$-$C_{20}$ aryl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9;
  wherein each said R5, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, R9 aryl (each of which that can be substituted, may optionally be substituted with R9)
  optionally R5 and R7 can be connected in a cyclic arrangement, where optionally such arrangement can have one or more heteroatoms selected from O, S, or, N, in the cyclic structure connecting R5 and R7;

(g) R6 is O, S, NR9, or NOR9;

(h) R7 is substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, OR9S(O)$_n$R9, C(=X1)R9, C(=X1)OR9, R9C(=X1)OR9, R9X2C(=X1)R9X2R9, C(=X1)N(R9)$_2$, N(R9)$_2$, N(R9)(R9S(O)$_n$R9), N(R9)C(=X1)R9, SR9, S(O)$_n$OR9, R9S(O)$_n$R9, $C_1$-$C_6$alkylOC(=O)$C_1$-$C_6$alkyl, OC$_1$-$C_6$ alkyl $C_1$-$C_{20}$ heterocyclyl, $C_1$-$C_6$alkyl$C_1$-$C_{20}$ heterocyclyl, $C_1$-$C_6$, alkylS(=N—CN)($C_1$-$C_6$alkyl), $C_1$-$C_6$alkylS(O)(=N—CN)($C_1$-$C_6$alkyl), $C_1$-$C_6$alkylS(O)$_n$($C_1$-$C_6$alkyl$C_1$-$C_{20}$heterocyclyl), $C_1$-$C_6$alkylS(O)(=N—CN)($C_1$-$C_6$ alkyl-$C_1$-$C_{20}$heterocyclyl), $C_1$-$C_6$alkylNH(C(=O)O$C_1$-$C_6$ alkyl), $C_1$-$C_6$ alkylC(=O)O$C_1$-$C_6$ alkyl, $C_1$-$C_6$alkyl($C_6$-$C_{20}$aryl)NH(C(=O)O$C_1$-$C_6$alkyl), $C_1$-$C_6$alkyl(S—$C_1$-$C_6$ alkyl)NH(C(=O)O$C_1$-$C_6$alkyl), $C_1$-$C_6$alkyl(S—$C_1$-$C_6$alkyl-$C_6$-$C_{20}$aryl)NH(C(=O)O$C_1$-$C_6$alkyl), $C_1$-$C_6$ alkyl(NHC(=O)O$C_1$-$C_6$alkyl$C_6$-$C_{20}$ aryl)NH(C(=O)O$C_1$-$C_6$alkyl), $C_1$-$C_6$alkyl(O$C_1$-$C_6$alkyl$C_6$-$C_{20}$aryl)NH(C(=O)O$C_1$-$C_6$alkyl), $C_1$-$C_6$alkylN($C_1$-$C_6$alkyl)(C(=O)O$C_1$-$C_6$alkyl), $C_1$-$C_6$alkylNH($C_1$-$C_6$alkyl), $C_6$-$C_{20}$arylS$C_1$-$C_6$haloalkyl, $C_1$-$C_6$alkyl-N($C_1$-$C_6$ alkyl)(C(=O)$C_1$-$C_6$alkyl$C_6$-$C_{20}$aryl), $C_1$-$C_6$alkylN($C_1$-$C_6$alkyl)($C_1$-$C_6$alkyl), $C_1$-$C_6$alkylN($C_1$-$C_6$ alkyl)(S(O)$_n$$C_1$-$C_6$ alkyl), $C_1$-$C_6$ alkylN($C_1$-$C_6$ alkyl)(S(O)$_n$$C_1$-$C_6$ alkenyl$C_6$-$C_{20}$ aryl), $C_1$-$C_6$ alkylN($C_1$-$C_6$ alkyl)(C(=O)$C_1$-$C_{20}$ heterocyclyl), $C_1$-$C_6$alkylN($C_1$-$C_6$alkyl)(C(=O)O$C_1$-$C_6$ alkyl$C_6$-$C_{20}$aryl), NH($C_1$-$C_6$ alkylS(O)$_n$$C_1$-$C_6$alkyl), NH($C_1$-$C_6$ alkylS(O)$_n$$C_6$-$C_{20}$ aryl), $C_1$-$C_6$alkyl(S(O)$_n$$C_1$-$C_6$ alkyl)(C(=O)$C_1$-$C_6$alkylS(O)$_n$($C_1$-$C_6$ alkyl), or R9S(O)$_n$(NZ)R9, wherein each said R7, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9), C(=X1)R9, C(=X1)OR9, C(=X1)N(R9)$_2$, =X2, N(R9)$_2$, S(=X2)$_n$R9, R9S(O)$_n$R9, S(O)$_n$N(R9)$_2$;

(i) R8 is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$R9, S(O)$_n$OR9, or R9S(O)$_n$R9, wherein each said R8, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(j) R9 (each independently) is H, CN, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, S(O)$_n$$C_1$-$C_6$ alkyl, N($C_1$-$C_6$alkyl)$_2$, wherein each said R9, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OC$_1$-$C_6$ alkyl, OC$_1$-$C_6$ haloalkyl, S(O)$_n$$C_1$-$C_6$alkyl, S(O)$_n$OC$_1$-$C_6$ alkyl, $C_6$-$C_{20}$ aryl, or $C_1$-$C_{20}$ heterocyclyl;

(k) R10 is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R10, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);

(l) n is (each independently) 0, 1, or 2;

(m) X1 is (each independently) O or S;

(n) X2 is (each independently) O, S, =NR9, or =NOR9; and (o) Z is CN, NO$_2$, $C_1$-$C_6$ alkyl(R9), C(=X1)N(R9)$_2$.

Formula One and its subparts (a) through (o) are hereafter referred to as "Embodiment A1".

In another embodiment of this molecule X is CR8.

In another embodiment of this molecule R1 is H.

In another embodiment of this molecule R2 is H.

In another embodiment of this molecule R3 is H.

In another embodiment of this molecule R4 is halo or unsubstituted $C_1$-$C_6$ alkyl.

In another embodiment of this molecule R4 is F, Cl, or unsubstituted $C_1$-$C_2$ alkyl.

In another embodiment of this molecule R4 is Cl, or CH$_3$.

In another embodiment of this molecule R5 is H, substituted or unsubstituted $C_1$-$C_6$ alkyl.

In another embodiment of this molecule R5 is a substituted $C_1$-$C_6$ alkyl that is substituted with a $C_3$-$C_{10}$ cycloalkyl.

In another embodiment of this molecule R5 is H, CH$_3$, CH$_2$-cyclopropyl, or CH$_2$CH$_3$.

In another embodiment of this molecule R6 is O.

In another embodiment of this molecule R7 is substituted or unsubstituted $C_1$-$C_6$ alkyl, OR9, or R9S(O)$_n$R9.

In another embodiment of this molecule R7 is a substituted $C_1$-$C_6$ alkyl wherein said substituent is one or more halos.

In another embodiment of this molecule R7 is a substituted $C_1$-$C_6$ alkyl wherein said substituent is one or more F or Cl or a combination thereof.

In another embodiment of this molecule R7 is a substituted $C_1$-$C_6$ alkyl wherein said substituent is one or more F.

In another embodiment of this molecule R7 is CH$_2$CF$_3$.

In another embodiment of this molecule R7 is an unsubstituted $C_1$-$C_6$ alkyl.

In another embodiment of this molecule R7 is CH(CH$_3$)$_2$, CH$_3$, C(CH$_3$)$_3$, or CH$_2$CH$_2$CH$_2$CH$_3$.

In another embodiment of this molecule R7 is OR9.

In another embodiment of this molecule R7 is O(unsubstituted $C_1$-$C_6$ alkyl).

In another embodiment of this molecule R7 is OC(CH$_3$)$_3$.
In another embodiment of this molecule R7 is R9S(O)$_n$R9.
In another embodiment of this molecule R7 is (unsubstituted C$_1$-C$_6$ alkyl)S(unsubstituted C$_1$-C$_6$ alkyl).
In another embodiment of this molecule R7 is CH$_2$CH(CH$_3$)SCH$_3$, CH$_2$CH$_2$SCH$_3$, CH(CH$_3$)$_2$SCH$_3$, or CH(CH$_3$)CH$_2$SCH$_3$.
In another embodiment of this molecule R8 is H or halo.
In another embodiment of this molecule R8 is H, F, or Cl.
In another embodiment of this molecule R8 is H or F.
In another embodiment of this molecule R9 is an unsubstituted C$_1$-C$_6$ alkyl.
In another embodiment of this molecule R10 is H or unsubstituted C$_1$-C$_6$ alkyl.
In another embodiment of this molecule R10 is H or CH$_3$.
In another embodiment of this molecule n is 0.
Combinations of these embodiments are also envisioned.

The molecules of Formula One will generally have a molecular mass of about 100 Daltons to about 1200 Daltons. However, it is generally preferred if the molecular mass is from about 120 Daltons to about 900 Daltons, and it is even more generally preferred if the molecular mass is from about 140 Daltons to about 600 Daltons.

The following scheme illustrates an approach to generating 2-methyl imidazolylamines. In step a of Scheme I, treatment of compounds of Formula III with ethyl acetimidate hydrochlorides of Formula IV wherein R5 is as defined in Embodiment A1 and R4 is methyl affords the corresponding acetamidines of Formula V. In step b of Scheme I, a-bromoketones of Formula II, wherein R1, R2, R3, R10, and X are as defined in Embodiment A1, can be treated with acetamidines of Formula V in the presence of an organic base, such as triethylamine, in a polar protic solvent such as ethyl alcohol to furnish N-Boc-aminoimidazoles of Formula Ia. When R5=H, carbamates of Formula Ia, wherein R1, R2, R3, R4, R10 and X are as defined in Embodiment A1, can be alkylated in the presence of a base such as sodium hydride and an alkyl halide such as iodomethane in an aprotic polar solvent such as N,N-dimethylformamide to yield compounds of Formula Ib, as shown in step e of Scheme I. Deprotection of carbamic acid tert-butyl esters of Formula Ia can be performed as in step c of Scheme I with trifluoroacetic acid (TFA) in a polar aprotic solvent such as dichloromethane (DCM) to yield the aminoimidazoles of Formula VIa, wherein R1, R2, R3, R4, R10, R5 and X are as defined in Embodiment A1. In step d of Scheme I, compounds of the Formula VIa can be treated with an acid chloride of Formula VII, wherein R7 is as defined in Embodiment A1, in the presence of both an organic base, such as N,N-dimethylaminopyridine (DMAP), and an inorganic base, such as potassium carbonate, in a polar aprotic solvent such as 1,2-dichloroethane (DCE) to afford compounds of Formula Ic.

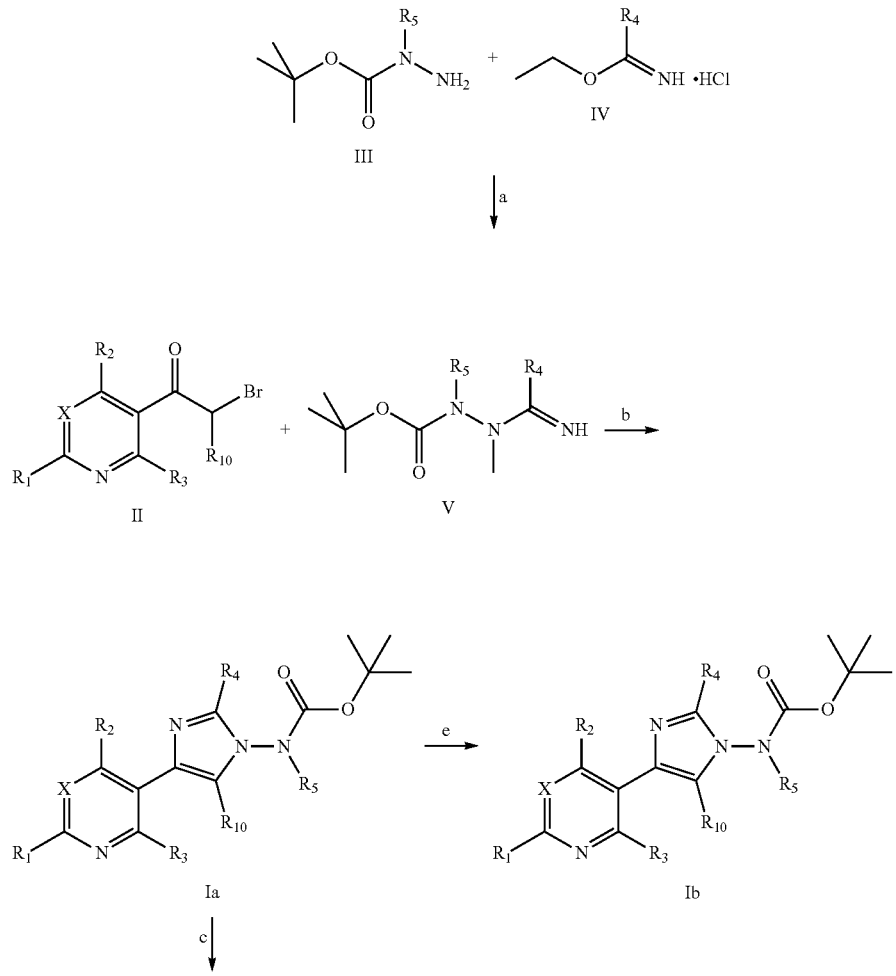

Scheme I

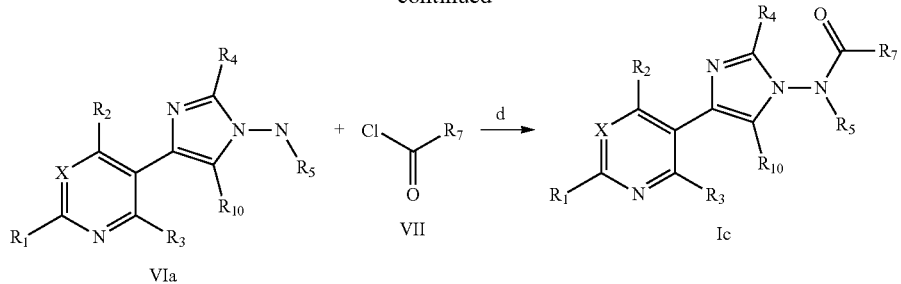

Another approach to generating imidazolylamines is illustrated in Scheme II. Diones of Formula VIII, wherein R1, R2, R3, R10 and X are as defined in Embodiment A1, can be treated with an aldehyde, such as acetaldehyde, a source of ammonia, such as ammonium acetate and a catalyst, such as indium(III)chloride, in a protic solvent, such as methanol to give compounds of Formula a. Compounds of Formula IX, wherein R1, R2, R3, R4, R10 and X are as defined in Embodiment A1, can be treated with a base such as sodium hydride in a solvent such as THF and addition of oxaziridines of Formula Xa to afford compounds of Formula Id, wherein R5 is H.

Scheme II

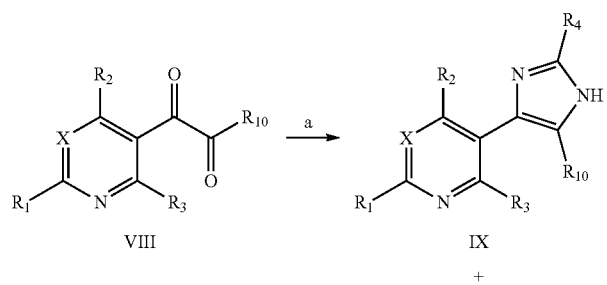

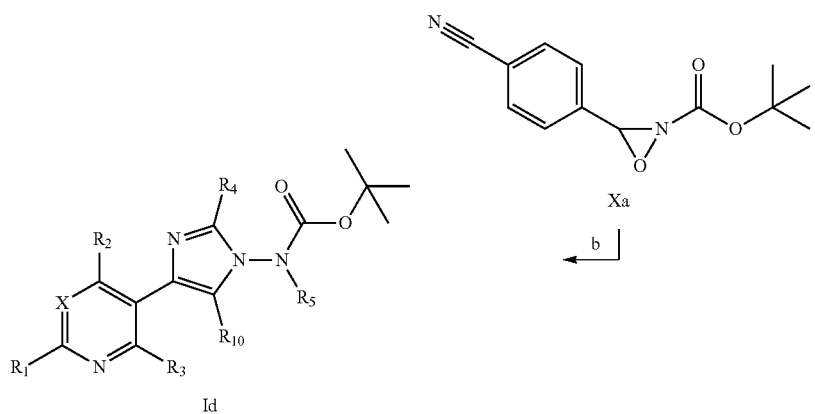

Another approach to generating imidazolylamines is illustrated in Scheme III. Substituted 2-aminoimidazoles of Formula XI were prepared according to the general procedure found in Li and co-workers, *J. Med. Chem.*, 2010, 53, 2409. Treatment of compounds of Formula XI, wherein R1, R2, R3, R10, and X are as defined in Embodiment A1, under Sandmeyer conditions leads to the formation of compounds of Formula XII, wherein R4 is halogen, as shown in step a of Scheme III. Hydrazones of Formula XII can be transformed to the corresponding amines of Formula VIb, wherein R5 is H when treated with hydrazine in a polar protic solvent such as 2-methoxyethanol, as shown in step b.

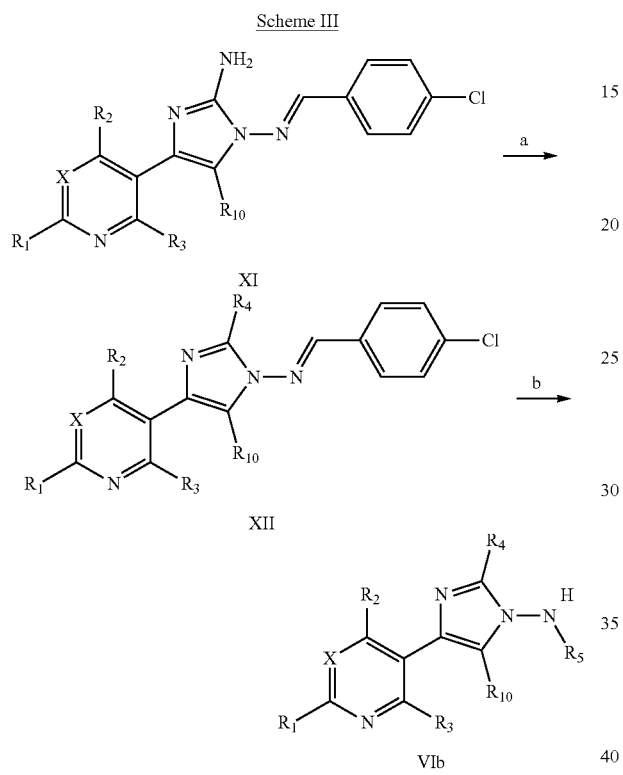

Another approach to generating imidazolylamines is illustrated in Scheme IV. Imidazoles of Formula XIII, wherein R4 and R10 are as defined in Embodiment A1 and Q is halogen (for example, bromine), can be treated with a base such as sodium hydride in a polar, aprotic solvent such as tetrahydrofuran and an aminating reagent such as oxaziridine of Formula Xb to afford compounds of Formula XIVa, as shown in step a of Scheme IV. Carbamates of Formula XIVa, can be alkylated in the presence of a base such as sodium hydride and an alkyl halide such as iodoethane in a polar aprotic solvent such as N,N-dimethylformamide to yield compounds of Formula XIVb, wherein R5 is alkyl, as shown in step b. Compounds of Formula XIVb, wherein R4, R5 and R10 are as defined in Embodiment A1, can be allowed to react under Suzuki coupling conditions with a boronic acid of Formula XV, wherein X, R1, R2 and R3 are as defined in Embodiment A1, to provide the heterocycle-coupled imidazole of Formula Ie, as shown in step c. When R4=H, compounds of Formula Ie can be halogenated in the presence of a base such as n-butyllithium in a polar aprotic solvent such as tetrahydrofuran and an electrophilic source of halogen such as hexachloroethane to yield 2-haloimidazoles of Formula If, wherein R4 is halogen and R1, R2, R3, R5, R10 and X are as defined in Embodiment A1, as shown in step d.

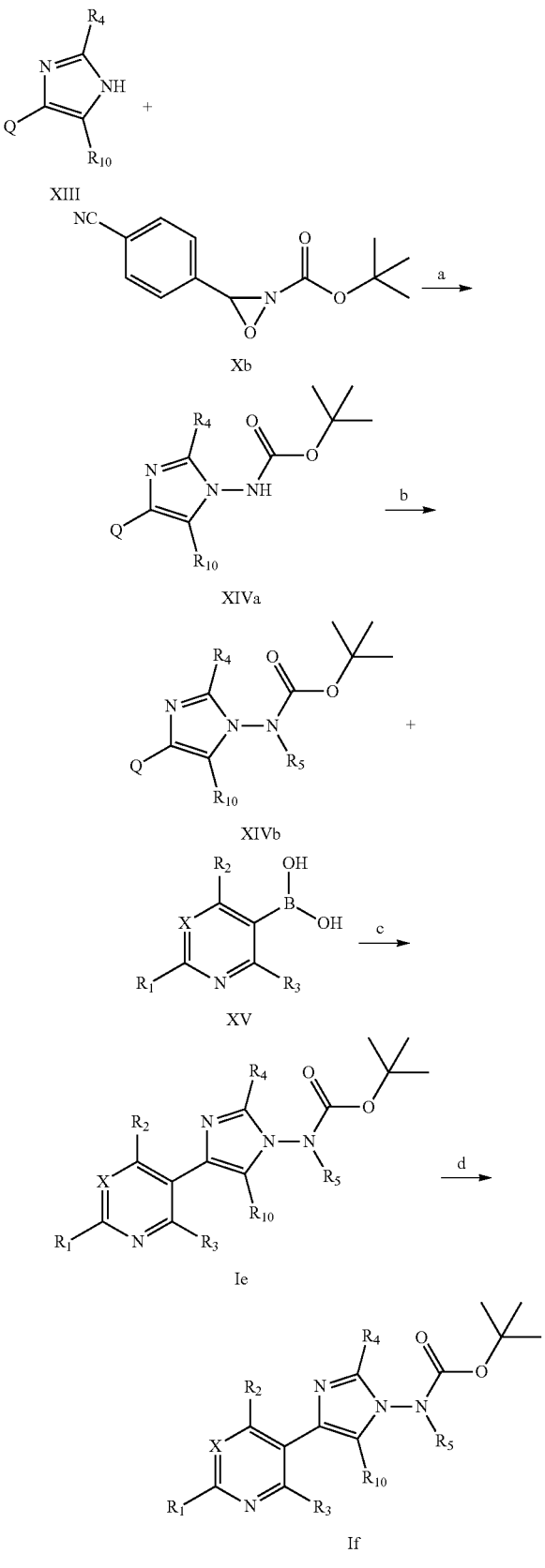

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. All NMR are in ppm (δ) and were recorded at 300, 400, or 600 MHz unless otherwise stated.

Example 1

Step 1: Preparation of N'-(1-Imino-ethyl)-N-methyl-hydrazinecarboxylic acid tert-butyl ester

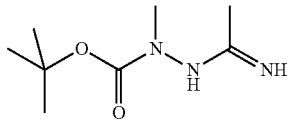

A solution of tert-butyl 1-methylhydrazinecarboxylate (10.0 g, 68.4 mmol), ethyl acetimidate hydrochloride (42.1 g, 342 mmol), and potassium carbonate (94.4 g, 684 mmol) in DMF (150 mL) was heated at 105° C. for 5 hours. The contents were cooled to 0° C. before the precipitated material was collected by vacuum filtration and resuspended in H₂O (100 mL). After 30 minutes of vigorous stirring, the remaining precipitate was collected and dried in a 45° C. vacuum oven overnight to yield the title compound as a white solid (7.56 g, 59.0%): mp 187-189° C.; ¹H NMR (400 MHz, DMSO-d₆) δ 6.28 (br s, 1H), 2.77 (s, 3H), 1.64 (s, 3H), 1.36 (s, 9H).

Example 1

Step 2: Preparation of Methyl-(2-methyl-4-pyridin-3-yl-imidazol-1-yl)-carbamic acid tert-butyl ester (Compound 3)

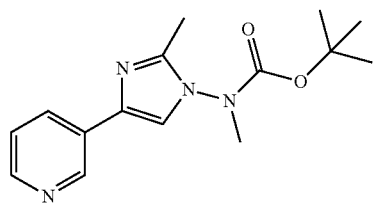 [SMILES: Cc1nc(-c2cccnc2)cn1N(C)C(=O)OC(C)(C)C]

To a solution of N'-(1-imino-ethyl)-N-methyl-hydrazinecarboxylic acid tert-butyl ester (5.00 g, 26.7 mmol) and triethylamine (9.30 mL, 66.8 mmol) in EtOH (100 mL) was added 2-bromo-1-pyridin-3-yl-ethanone hydrobromide (8.99 g, 32.0 mmol), portionwise. The contents were heated at 80° C. for 3 hours before the solvent was removed under reduced pressure and the residue was purified via silica gel chromatography (DCM:MeOH, 10:1) to afford the title compound as an orange oil (1.55 g, 20.1%): ¹H NMR (400 MHz, CDCl₃) δ 8.92 (d, J=2.4 Hz, 1H), 8.43 (dd, J=4.9, 1.4 Hz, 1H), 8.03 (dt, J=8.3, 1.6 Hz, 1H), 7.28 (dd, J=7.7, 4.8 Hz, 1H), 7.21 (s, 1H), 3.38 (s, 3H), 2.36 (s, 3H), 1.43 (s, 9H); ESIMS m/z 289 [(M+H)]⁺.

Example 1

Step 3: Preparation of Methyl-(2-methyl-4-pyridin-3-yl-imidazole-1-yl)-amine

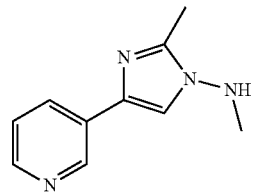

Method A:

A solution of methyl-(2-methyl-4-pyridin-3-yl-imidazol-1-yl)-carbamic acid tert-butyl ester (1.50 g, 5.20 mmol) and trifluoroacetic acid (0.40 mL, 5.20 mmol) in DCM (5 mL) was stirred under ambient conditions for 3 hours. The solvent was removed under reduced pressure and the residue was resuspended in DCM (10 mL) before the addition of triethylamine (1.45 mL, 10.4 mmol). After stirring for 10 minutes the solvent was removed and the residue was purified via silica gel chromatography (DCM:MeOH, 10:1) to afford an inseparable mixture of the title compound and triethylammonium salts (822 mg). The mixture was used without further purification in the subsequent reactions.

Method B:

A solution of tert-butyl methyl(2-methyl-4-(pyridin-3-yl)-1H-imidazol-1-yl) carbamate (2.7 g, 9.4 mmol) in dichloromethane (50 mL) was treated with HCl in dioxane (4M, 20 mL). The mixture was stirred overnight at room temperature. The precipitate was filtered off to give the title compound as a brown solid (1.15 g, 54.5%): ¹H NMR (300 MHz, DMSO-d₆) δ 9.41-9.32 (m, 1H), 8.82-8.56 (m, 3H), 7.97-7.89 (m, 1H), 2.85 (s, 3H), 2.67 (d, J=3.0 Hz, 3H); ESIMS m/z 189 [(M+H)]⁺.

N-Ethyl-2-methyl-4-(pyridin-3-yl)-1H-imidazol-1-amine was prepared in accordance with the procedures disclosed in Example 1, Step 3, Method B: ¹H NMR (300 MHz, DMSO-d₆) δ 9.32 (s, 1H), 8.76-8.69 (m, 2H), 8.57-8.46 (m, 1H), 7.81 (s, 1H), 3.12-3.03 (m, 2H), 2.63 (s, 3H), 1.06 (t, 3H, J=7.2 Hz); ESIMS m/z 203 [(M+H)]⁺.

N-(Cyclopropylmethyl)-2-methyl-4-(pyridin-3-yl)-1H-imidazol-1-amine was prepared in accordance with the procedures disclosed in Example 1, Step 3, Method B: ¹H NMR (300 MHz, DMSO-d₆) δ 9.26 (s, 1H), 8.74-8.72 (m, 1H), 8.67-8.59 (m, 1H), 8.51-8.46 (m, 1H), 7.81 (s, 1H), 2.95 (d, 2H, J=7.2 Hz), 2.66 (s, 3H), 0.93-0.86 (m, 1H), 0.46-0.43 (m, 2H), 0.07-0.06 (m, 2H); ESIMS m/z 229 [(M+H)]⁺.

4-(5-Fluoropyridin-3-yl)-N,2-dimethyl-1H-imidazol-1-amine was prepared in accordance with the procedures disclosed in Example 1, Step 3, Method B: ¹H NMR (300 MHz, CD₃OD) δ 9.05 (s, 1H), 8.84 (s, 1H), 8.47-8.44 (m, 2H), 2.97 (s, 3H), 2.74 (s, 3H); ESIMS m/z 207 [(M+H)]⁺.

N-Ethyl-4-(5-fluoropyridin-3-yl)-2-methyl-1H-imidazol-1-amine was prepared in accordance with the procedures disclosed in Example 1, Step 3, Method B: $^1$H NMR (300 MHz, CD$_3$OD) δ 8.99 (s, 1H), 8.80 (s, 1H), 8.41-8.35 (m, 2H), 3.26 (q, J=7.2 Hz, 2H), 2.74 (s, 3H), 1.19 (t, 3H, J=7.2 Hz); ESIMS m/z 221 [(M+H)]$^+$.

N-(Cyclopropylmethyl)-4-(5-fluoropyridin-3-yl)-2-methyl-1H-imidazol-1-amine was prepared in accordance with the procedures disclosed in Example 1, Step 3, Method B: $^1$H NMR (300 MHz, CD$_3$OD) δ 8.965 (s, 1H), 8.746 (s, 1H), 8.39-8.30 (m, 2H), 3.08-3.05 (m, 2H), 2.77 (s, 3H), 1.08-0.95 (m, 1H), 0.56-0.56 (m, 2H), 0.19-0.15 (m, 2H); ESIMS m/z 247 [(M+H)]$^+$.

Example 1

Step 4: Preparation of N-Methyl-N-(2-methyl-4-pyridin-3-yl-imidazol-1-yl)-3-methylsulfanyl-butramide (Compound 2)

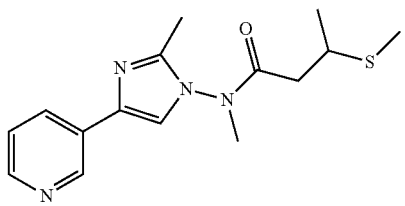 [SMILES: CSC(C)CC(=O)N(C)n1cc(-c2cccnc2)nc1C]

A solution of methyl-(2-methyl-4-pyridin-3-yl-imidazole-1-yl)-amine (400 mg, 2.13 mmol), 3-methylsulfanyl-butyryl chloride (649 mg, 4.25 mmol), DMAP (260 mg, 2.13 mmol), and potassium carbonate (881 mg, 6.38 mmol) in DCE (5 mL) was heated at 80° C. for 6 hours. The solvent was removed under reduced pressure and the residue was purified via reverse phase chromatography (0 to 100% acetonitrile/water) to furnish the title compound as a brown oil (290 mg, 44.8%): $^1$H NMR (400 MHz, CDCl$_3$) δ 8.94 (br s, 1H), 8.47 (dd, J=5.0, 1.4 Hz, 1H), 8.04 (dt, J=8.2, 1.5 Hz, 1H), 7.36-7.27 (m, 2H), 3.39 (s, 3H), 3.25-3.18 (m, 1H), 2.38 (s, 3H), 2.27-2.19 (m, 2H), 2.02 (s, 3H), 1.24 (d, J=6.2 Hz, 3H); ESIMS m/z 304 [(M+H)]$^+$.

Compounds 1, 5-38 were made in accordance with the procedures disclosed in Example 1.

Example 2

Step 1: Preparation of 3-(2,5-Dimethyl-1H-imidazol-4-yl)pyridine

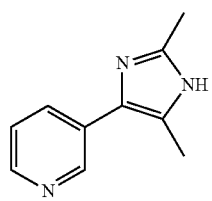

The compound was prepared following the general procedure found in: Sharma, S. D.; Hazarika, P.; Konwar, D. *Tetrahedron Lett.* 2008, 49, 2216. 1-Pyridin-3-yl-propane-1,2-dione (prepared as described in Knaus, E. E.; Avasthi, K.; Redda, K.; Benderly, A. *Can. J. Chem.* 1980, 58(2), 130; 0.50 g, 3.35 mmol), ammonium acetate (0.517 g, 6.71 mmol) and indium (III) chloride (0.074 g, 0.033 mmol) were weighed into a 50 mL round bottomed flask. Methanol (MeOH, 7 mL) and acetaldehyde (0.148 g, 0.190 mL, 3.35 mmol) were added via syringe and the cloudy mixture was stirred vigorously overnight. Analysis by TLC CH$_2$Cl$_2$:MeOH/10:1 indicated that some starting material remained. Additional ammonium acetate (0.517 g, 6.71 mmol), indium (III) chloride (0.074 g, 0.033 mmol) and acetaldehyde (0.148 g, 0.190 mL, 3.35 mmol) were added and again allowed to stir overnight. The mixture was filtered through paper with MeOH to remove sediment and concentrated to low volume. The residue was purified via flash silica gel chromatography, CH$_2$Cl$_2$:MeOH/10:1 to afford a low Rf-spot-compound. The material was dissolved in a minimum amount of CH$_2$Cl$_2$ and treated with sat. NaHCO$_3$. The resulting precipitate was collected by filtration and washed with water and CH$_2$Cl$_2$ and dried to give 0.105 g of a light yellow powder. The layers of the filtrate were separated and the aqueous phase was extracted repeatedly with CH$_2$Cl$_2$ and ethyl acetate (EtOAc). The combined extracts were dried over Na$_2$SO$_4$, filtered and concentrated to give an additional 0.06 g of the title compound as a yellow orange solid (0.165 g, 28%): mp 179-181° C.; $^1$H NMR (300 MHz, CDCl$_3$) δ 8.85 (bs, 1H), 8.46 (d, J=4.1 Hz, 1H), 7.99 (bs, 1H), 7.31 (dd, J=7.7, 4.7 Hz, 1H), 2.44 (s, 6H); ESIMS m/z 174 [(M+H)]$^+$ and 172 [(M–H)]$^-$.

Example 2

Step 2: Preparation of (2,5-Dimethyl-4-pyridin-3-yl-imidazol-1-yl)-carbamic acid tert-butyl ester (Compound 4)

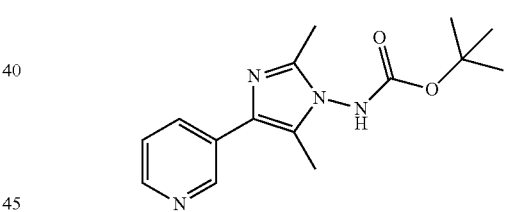

3-(2,5-Dimethyl-1H-imidazol-4-yl)-pyridine (0.035 g, 0.220 mmol) was weighed into an oven dried, nitrogen swept 10 mL round bottomed flask. Tetrahydrofuran (THF, 1 mL) was added via syringe and the resulting slurry cooled on an ice bath under nitrogen and treated with sodium hydride (0.0097 g, 0.242 mmol 60% dispersion in oil) with stirring. After 10 minutes, 3-(4-cyano-phenyl)-oxaziridine-2-carboxylic acid tert-butyl ester (0.052 g, 0.212 mmol) was added as a solid and the thick yellow slurry allowed to warm to room temperature and stir for 2 hours. The crude reaction mixture was loaded directly onto a flash silica gel column and eluted with CH$_2$Cl$_2$:MeOH/10:1 giving (2,5-dimethyl-4-pyridin-3-yl-imidazol-1-yl)-carbamic acid tert-butyl ester as a light yellow oil as a 5:1 mixture with its regioisomer (0.027 g, 46%): IR (film) 3389, 2978, 2930, 1730, 1478, 1275, 1252, 1156, 1017, 951, 711, 573 cm$^{-1}$; $^1$H NMR (300 MHz, DMSO, Major isomer) δ 10.41 (s, 1H), 8.81 (s, 1H), 8.39 (s, 1H), 7.95 (d, J=8.0 Hz, 1H), 7.44-7.28 (m, 1H), 2.21 (s, 3H), 2.18 (s, 3H), 1.46 (s, 9H); ESIMS m/z 289 [(M+H)]$^+$ and 287 [(M–H)]$^-$.

Example 3

Preparation of tert-Butyl (2-methyl-4-(pyridin-3-yl)-1H-imidazol-1-yl)-carbamate

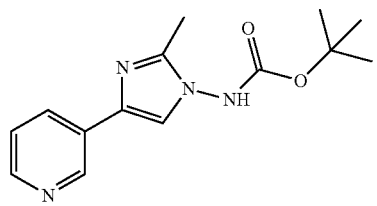 [SMILES: Cc1nc(-c2cccnc2)cn1NC(=O)OC(C)(C)C]

To a mixture of ethyl acetimidate hydrochloride (2.0 g, 16.20 mmol) and triethylamine (3.28 g, 32.4 mmol) in ethanol (40 mL) was added a solution of tert-butyl hydrazinecarboxylate (2.14 g, 16.20 mmol) in ethanol (10 mL) at room temperature. The resulting mixture was stirred at room temperature overnight. Then to the mixture was added a solution of 2-bromo-1-(pyridin-3-yl)ethanone hydrobromide (5.0 g, 17.9 mmol) and triethylamine (4.9 g, 48.6 mmol) in ethanol (20 mL). The reaction mixture was stirred at room temperature for 5 hours then heated to reflux overnight. The solvent was removed under reduced pressure and the residue was purified via silica gel chromatography (dichloromethane:methanol, 10:1) to give the title compound as an orange oil (0.76 g, 17.3%): $^1$H NMR (300 MHz, CDCl$_3$) δ 8.87 (s, 1H), 8.45 (d, 1H, J=6.3 Hz), 8.43 (s, 1H), 8.05 (d, 1H, J=6.3 Hz), 7.33-7.25 (m, 2H), 2.37 (s, 3H), 1.51 (s, 9H); ESIMS m/z 275 [(M+H)]$^+$.

Example 4

Preparation of tert-Butyl methyl(2-methyl-4-(pyridin-3-yl)-1H-imidazol-1-yl) carbamate (Compound 3) (another way of making Compound 3)

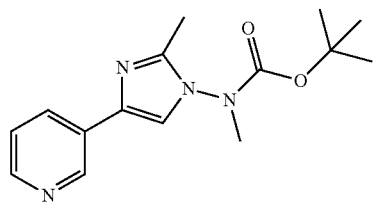 [SMILES: Cc1nc(-c2cccnc2)cn1N(C)C(=O)OC(C)(C)C]

To a solution of tert-butyl 2-methyl-4-(pyridin-3-yl)-1H-imidazol-1-ylcarbamate (2.0 g, 7.3 mmol) in dry DMF (15 mL) at 0° C. was added sodium hydride (0.35 g, 8.7 mmol, 60% dispersion in oil). The reaction was stirred at 0° C. for 30 minutes and then methyl iodide (1.55 g, 10.9 mmol) was added portionwise. The reaction mixture was stirred at 0° C. for 3 hours before it was warmed to ambient temperature. The reaction was extracted with ethyl acetate (15 mL×2). The organic layer was washed with brine (10 mL), dried over anhydrous sodium sulfate, filtered and concentrated to give the title compound (1.18 g, 56.2%) as an orange oil, which was used in the next step without further purification: $^1$H NMR (300 MHz, CDCl$_3$): δ 8.96 (s, 1H), 8.49 (s, 1H), 8.16-8.13 (m, 1H), 7.38-7.36 (m, 2H), 3.36 (s, 3H), 2.35 (s, 3H), 1.44 (s, 9H); ESIMS m/z 289 [(M+H)]$^+$.

tert-Butyl ethyl(2-methyl-4-(pyridin-3-yl)-1H-imidazol-1-yl)carbamate was prepared in accordance with the procedures disclosed in Example 4: $^1$H NMR (300 MHz, CDCl$_3$) δ 8.94 (s, 1H), 8.48-8.46 (m, 1H), 8.09-8.05 (m, 1H), 7.31-7.29 (m, 1H), 7.20 (s, 1H), 3.86-3.67 (m, 2H), 2.34 (s, 3H), 1.44 (s, 9H), 1.21 (t, J=7.2 Hz, 3H); ESIMS m/z 303 [(M+H)]$^+$.

tert-Butyl (cyclopropylmethyl)(2-methyl-4-(pyridin-3-yl)-1H-imidazol-1-yl)carbamate was prepared in accordance with the procedures disclosed in Example 4: $^1$H NMR (300 MHz, CDCl$_3$) δ 8.94 (s, 1H), 8.48-8.46 (m, 1H), 8.10-8.06 (m, 1H), 7.31-7.28 (m, 1H), 7.25 (s, 1H), 3.59-3.54 (m, 2H), 2.37 (s, 3H), 1.44 (s, 9H), 1.05-0.93 (m, 1H), 0.56-0.53 (m, 2H), 0.20-0.15 (m, 2H); ESIMS m/z 329 [(M+H)]$^+$.

tert-Butyl (4-(5-fluoropyridin-3-yl)-2-methyl-1H-imidazol-1-yl)(methyl)carbamate was prepared in accordance with the procedures disclosed in Example 4: $^1$H NMR (300 MHz, CDCl$_3$) δ 8.72 (s, 1H), 8.31 (d, J=2.7 Hz, 1H), 7.83-7.78 (m, 1H), 7.27 (s, 1H), 3.36 (s, 3H), 2.34 (s, 3H), 1.44 (s, 9H); ESIMS m/z 307 [(M+H)]$^+$.

tert-Butyl ethyl(4-(5-fluoropyridin-3-yl)-2-methyl-1H-imidazol-1-yl)carbamate was prepared in accordance with the procedures disclosed in Example 4: $^1$H NMR (300 MHz, CDCl$_3$) δ 8.73 (s, 1H), 8.32-8.31 (m, 1H), 7.84-7.80 (m, 1H), 7.23 (s, 1H), 3.87-3.70 (m, 2H), 2.34 (s, 3H), 1.45 (s, 9H), 1.21 (t, J=7.2 Hz, 3H); ESIMS m/z 321 [(M+H)]$^+$.

tert-Butyl (cyclopropylmethyl)(4-(5-fluoropyridin-3-yl)-2-methyl-1H-imidazol-1-yl)carbamate was prepared in accordance with the procedures disclosed in Example 4: $^1$H NMR (300 MHz, CDCl$_3$) δ 8.7 s (s, 1H), 8.30-8.29 (m, 1H), 7.85-7.80 (m, 1H), 7.27 (s, 1H), 3.57-3.54 (m, 2H), 2.37 (s, 3H), 1.44 (s, 9H), 1.02-0.93 (m, 1H), 0.55-0.53 (m, 2H), 0.21-0.17 (m, 2H); ESIMS m/z 347 [(M+H)]$^+$.

Example 5

Step 1: Preparation of E-2-Chloro-N-(4-chlorobenzylidene)-4-(pyridin-3-yl)-1H-imidazol-1-amine

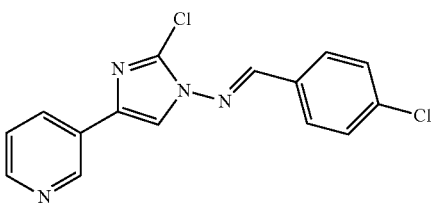 [SMILES: Clc1ccc(/C=N/n2cc(-c3cccnc3)nc2Cl)cc1]

To a solution of (E)-N$^1$-(4-chlorobenzylidene)-4-(pyridin-3-yl)-1H-imidazole-1,2-diamine (5.3 g, 18 mmol) and CuCl (1.79 g, 18 mmol) in acetonitrile (100 mL) was added isopentyl nitrite (3.15 g, 27 mmol) at 0° C. The reaction mixture was stirred for 1 hour at room temperature, and then heated to 70° C. for 3 hours. The solvent was removed in vacuum, the residue was purified by column chromatography (petroleum ether: ethyl acetate=2:1) to give the title compound (258 mg, 4%) as a white solid: $^1$H NMR (300 MHz, CDCl$_3$) δ 8.99 (s, 1H), 8.55-8.54 (m, 1H), 8.42 (s, 1H), 8.17-8.13 (m, 1H), 7.86-7.83 (m, 3H), 7.50 (d, J=8.4 Hz, 2H), 7.36-7.31 (m, 1H); ESIMS m/z 317 [(M+H)]$^+$.

Example 5

Step 2: Preparation of 2-Chloro-4-(pyridin-3-yl)-1H-imidazol-1-amine

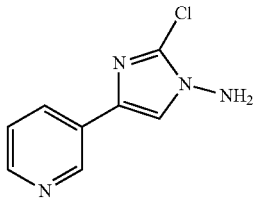 [SMILES: Nn1cc(-c2cccnc2)nc1Cl]

To a solution of E-2-Chloro-N-(4-chlorobenzylidene)-4-(pyridin-3-yl)-1H-imidazol-1-amine (210 mg, 0.66 mmol) in 2-methoxyethanol (5 mL) was added 80% hydrazine hydrate (0.5 mL). The reaction mixture was heated to 130° C. for 1 hour and then the reaction mixture was concentrated. The residue was purified by column chromatography (petroleum ether: ethyl acetate=1:1) to give the title compound (100 mg, 78%) as a yellow solid: $^1$H NMR (300 MHz, CDCl$_3$) δ 8.91 (s, 1H), 8.50-8.49 (m, 1H), 8.06-8.03 (m, 1H), 7.43 (s, 1H), 7.34-7.30 (m, 1H), 4.87 (br, 2H); ESIMS m/z 195 [(M+H)]$^+$.

Example 5

Step 3: Preparation of N-(2-Chloro-4-(pyridin-3-yl)-1H-imidazol-1-yl)acetamide (Compound 39)

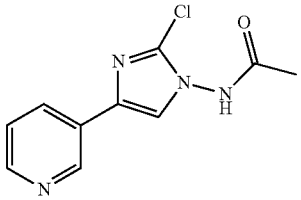 [SMILES: CC(=O)Nn1cc(-c2cccnc2)nc1Cl]

To a solution of 2-Chloro-4-(pyridin-3-yl)-1H-imidazol-1-amine (30 mg, 0.15 mmol) and triethylamine (15 mg, 0.15 mmol) in dichloromethane (5 mL) was added acetyl chloride (12 mg, 0.15 mmol) at 0° C. The reaction mixture was stirred for 30 minutes at 0° C. The solvent was removed in vacuum and the residue was purified by prep-TLC (petroleum ether: ethyl acetate=1:2) to give the title compound (10 mg, 27%) as a yellow solid: mp 129-131° C.; $^1$H NMR (300 MHz, CDCl$_3$) δ 10.69 (br, 1H), 8.81-8.80 (m, 1H), 8.44-8.43 (m, 1H), 8.02-8.00 (m, 1H), 7.33 (br s, 2H), 2.20 (s, 3H); ESIMS m/z 237 [(M+H)]$^+$.

Example 6

Step 1: Preparation of tert-Butyl (4-bromo-1H-imidazol-1-yl)carbamate

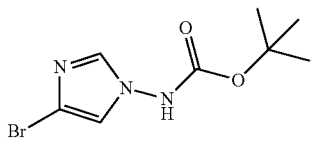

4-Bromo-1H-imidazole (3.2 g, 21.8 mmol) was weighed into a 500 mL round bottomed flask equipped with a magnetic stir bar under a nitrogen atmosphere. Anhydrous N,N-dimethylformamide (DMF, 12 mL) was added and the mixture was placed on ice. After 10 minutes the mixture was treated with sodium hydride (0.840 g, 21.0 mmol 60% dispersion in oil). After 5 minutes, the ice bath was removed and the reaction warmed to room temperature. After 15 minutes of vigorous stirring the ice bath was re-inserted and 3-(4-cyanophenyl)-oxaziridine-2-carboxylic acid tert-butyl ester (1.92 g, 7.80 mmol) was added. The reaction was vigorously stirred for 5 minutes and the ice bath was removed. After 5 minutes the mixture was diluted with saturated sodium bicarbonate and extracted with ethyl acetate. The organics were washed with dilute sodium carbonate, dried over sodium sulfate, and concentrated. The residue was purified using silica gel chromatography (0-5% methanol/dichloromethane) to afford the title compound (1.16 g, 4.43 mmol, 57%) as a yellow oil: $^1$H NMR (400 MHz, CDCl$_3$) δ 9.22 (s, 1H), 7.36 (d, J=1.5 Hz, 1H), 6.97 (d, J=1.5 Hz, 1H), 1.48 (s, 9H); ESIMS m/z 262 ([M]$^+$), 260 ([M−2]$^−$).

Example 6

Step 2: Preparation of tert-Butyl (4-bromo-1H-imidazol-1-yl)(ethyl)carbamate

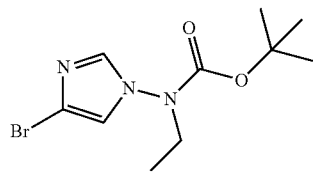 [SMILES: CCN(C(=O)OC(C)(C)C)n1cnc(Br)c1]

tert-Butyl (4-bromo-1H-imidazol-1-yl)carbamate (1.16 g, 4.43 mmol) was dissolved in N,N-dimethylformamide (DMF, 12 mL) and treated with sodium hydride (0.310 g, 7.75 mmol, 60% dispersion in oil). After 45 minutes, the mixture was cooled on an ice bath and was treated with iodoethane (0.828 g, 5.31 mmol). The ice bath was removed after five minutes of stirring and the reaction was stirred for an additional 90 minutes. The reaction mixture was diluted with aqueous potassium carbonate (50 mL, 5% w/w) and the product was extracted with ethyl acetate. The organics were washed with 5% aqueous potassium carbonate and brine and dried over sodium sulfate. The organic layer was concentrated and the residue was purified using silica gel chromatography (0-10% methanol/dichloromethane) to afford the title compound (1.023 g, 3.53 mmol, 80%) as a yellow oil: $^1$H NMR (400 MHz, CDCl$_3$) δ 7.37 (d, J=1.5 Hz, 1H), 6.93 (d, J=1.5 Hz, 1H), 3.71 (q, J=7.2 Hz, 2H), 1.44 (s, 9H), 1.16 (t, J=7.2 Hz, 3H); ESIMS m/z 290 ([M+H]$^+$).

Example 6

Step 3: Preparation of tert-Butyl ethyl(4-(pyridin-3-yl)-1H-imidazol-1-yl)carbamate (Compound 40)

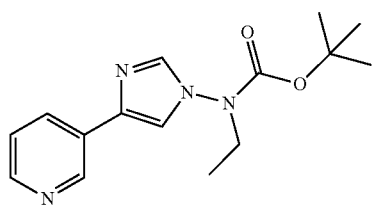 [SMILES: CCN(C(=O)OC(C)(C)C)n1cnc(-c2cccnc2)c1]

tert-Butyl (4-bromo-1H-imidazol-1-yl)(ethyl)carbamate (253.7 mg, 0.874 mmol), pyridin-3-ylboronic acid (113 mg, 0.918 mmol), potassium carbonate (329 mg, 2.39 mmol), water (0.870 mL), absolute ethanol (1.74 mL), and toluene (3.50 mL) were placed into a 10 mL round bottomed flask equipped with condenser and magnetic stirrer. The atmosphere was flushed with nitrogen and tetrakis triphenylphosphine palladium (30.0 mg, 0.026 mmol) was added. The mixture was heated to 110° C. and stirred for 16 hours. The reaction was cooled, the organic layer set aside, and the aqueous layer was extracted with ethyl acetate. All organics were combined, dried over sodium sulfate, and concentrated. The residue was purified using silica gel chromatography (0-25% methanol/dichloromethane) to afford the title compound (81 mg, 0.28 mmol, 32%) as a yellow oil: $^1$H NMR (400 MHz, CD$_3$CN) δ 9.00 (d, J=2.5 Hz, 1H), 8.46 (d, J=4.8 Hz, 1H), 8.11 (m, 1H), 7.67 (d, J=1.3 Hz, 1H), 7.61 (d, J=1.2 Hz, 1H), 7.36 (m, 1H), 3.76 (q, J=7.1 Hz, 2H), 1.45 (s, 9H), 1.17 (t, J=7.2 Hz, 3H); ESIMS m/z 289 ([M+H]$^+$).

Example 6

Step 4: Preparation of tert-Butyl (2-chloro-4-(pyridin-3-yl)-1H-imidazol-1-yl)(ethyl)carbamate (Compound 41)

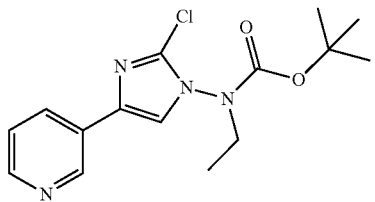 [SMILES: CCN(C(=O)OC(C)(C)C)n1cc(-c2cccnc2)nc1Cl]

A vacuum dried 25 mL round bottomed flask equipped with a magnetic stir bar and containing tert-butyl ethyl(4-(pyridin-3-yl)-1H-imidazol-1-yl)carbamate (77 mg, 0.267 mmol) was charged with anhydrous tetrahydrofuran (THF, 3 mL) and cooled to −78° C. N-butyllithium (0.25 mL 0.675 mmol, 2.5 M in hexanes) was added and the mixture was stirred for 15 minutes. Hexachloroethane (189 mg, 0.80 mmol) dissolved in anhydrous THF (1 mL) was added dropwise to the reaction mixture while maintaining a temperature of −78° C. After stirring for 1 hour, the reaction was allowed to warm to room temperature. The reaction mixture was loaded directly on a silica gel column and the THF was removed in a vacuum oven. The crude product was purified using silica gel chromatography (0-25% methanol/dichloromethane) to afford the title compound (3 mg, 0.009 mmol, 3.5%) as a yellow oil: $^1$H NMR (600 MHz, CDCl$_3$) δ 8.92 (d, J=1.6 Hz, 1H), 8.50 (dd, J=4.8, 1.5 Hz, 1H), 8.06 (dt, J=7.9, 2.0 Hz, 1H), 7.33-7.27 (m, 2H), 3.89 (dq, J=14.5, 7.3 Hz, 1H), 3.68 (dq, J=14.3, 7.2 Hz, 1H), 1.44 (s, 9H), 1.22 (t, J=7.2 Hz, 3H); $^{13}$C NMR (151 MHz, CDCl$_3$) δ 152.90, 148.47, 146.02, 136.07, 134.08, 131.81, 128.79, 123.36, 117.66, 83.23, 45.32, 28.04, 13.03; ESIMS m/z 323 ([M+H]$^+$).

Example A

Bioassays on Green Peach Aphid ("GPA") (*Myzus Persicae*) (Myzupe)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, *papaya*, peppers, sweet potatoes, tomatoes, watercress, and zucchini, among other plants. GPA also attacks many ornamental crops such as carnation, *chrysanthemum*, flowering white cabbage, poinsettia, and roses. GPA has developed resistance to many pesticides.

Certain molecules disclosed in this document were tested against GPA using procedures described in the following example. In the reporting of the results, the "Table 3: GPA (MYZUPE) and sweetpotato whitefly-crawler (BEMITA) Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in H$_2$O to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

Corrected % Control=100*(X−Y)/X where
X=No. of live aphids on solvent check plants and
Y=No. of live aphids on treated plants The results are indicated in the table entitled "Table 4. Biological Data for GPA (MYZUPE) and sweetpotato whitefly-crawler (BEMITA)" (See Table Section).

Example B

Insecticidal Test for Sweetpotato Whitefly-Crawler (*Bemisia tabaci*) (BEMITA) in Foliar Spray Assay Cotton plants grown in 3-inch pots, with 1 small (3-5 cm) true leaf, were used as test substrate. The plants were placed in a room with whitefly adults. Adults were allowed to deposit eggs for 2-3 days. After a 2-3 day egg-laying period, plants were taken from the adult whitefly room. Adults were blown off leaves using a hand-held Devilbiss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in H$_2$O to obtain a test solution at 200 ppm. A hand-held Devilbiss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Insecticidal activity was measured by using Abbott's correction formula and presented in "Table 4. Biological Data for GPA (MYZUPE) and sweetpotato whitefly-crawler (BEMITA)" (see column "BEMITA"):

Corrected % Control=100*(X−Y)/X where
X=No. of live nymphs on solvent check plants
Y=No. of live nymphs on treated plants Pesticidally Acceptable Acid Addition Salts, Salt Derivatives, Solvates, Ester Derivatives, Polymorphs, Isotopes and Radionuclides Molecules of Formula One may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the invention disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

Molecules of Formula One may also be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, or virucidal properties. Additionally, the molecules of Formula One may also be used in combination (such as, in a compositional mixture, or a simultaneous or sequential application) with compounds that are antifeedants, bird repellents, chemosterilants, herbicide safeners, insect attractants, insect repellents, mammal repellents, mating disrupters, plant activators, plant growth regulators, or synergists. Examples of such compounds in the above groups that may be used with the Molecules of Formula One are—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3, 6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlomidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, prolufarin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Biopesticides

Molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Molecules of Formula One may also be used in combination (such as in a compositional mixture, or a simultaneous or sequential application) with one or more of the following:
1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;

4. 4-[[(6-chloro-3-pyridinyl)methyl]cyclopropylamino]-2 (5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl) ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)] phenyl mesylate; and
20. N-Ethyl-2,2-dichloro-1-methylcyclopropanecarboxamide-2-(2,6-dichloro-alpha,alpha,alpha-trifluoro-p-tolyl) hydrazone.

Synergistic Mixtures

Molecules of Formula One may be used with certain active compounds to form synergistic mixtures where the mode of action of such compounds compared to the mode of action of the molecules of Formula One are the same, similar, or different. Examples of modes of action include, but are not limited to: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs). Generally, weight ratios of the molecules of Formula One in a synergistic mixture with another compound are from about 10:1 to about 1:10, in another embodiment from about 5:1 to about 1:5, and in another embodiment from about 3:1, and in another embodiment about 1:1.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph no 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. beetles, earwigs, cockroaches, flies, aphids, scales, whiteflies, leafhoppers, ants, wasps, termites, moths, butterflies, lice, grasshoppers, locusts, crickets, fleas, *thrips*, bristletails, mites, ticks, nematodes, and symphylans.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., Aulacophora spp., *Bruchus* spp., Cerosterna spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus*

*cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile,* and *Zabrus tenebrioides.*

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis,* and *Supella longipalpa.*

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrusi ovis, Oscinella frit, Pegomya betae, Psila rosae, Rhagoletis cerasi, Rhagoletis pomonella, Rhagoletis mendax, Sitodiplosis mosellana,* and *Stomoxys calcitrans.*

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus disperses, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relatives, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile.*

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias*

*vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera fruglperda, Spodoptera eridania, Thecla basilides, Tineola bisselliella, Trichoplusia ni, Tuta absoluta, Zeuzera coffeae,* and *Zeuzera pyrina.*

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans.*

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis,* and *Taeniothrips rhopalantennalis, Thrips hawaiiensis, Thrips nigropilosus, Thrips orientalis, Thrips tabaci.*

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae,* and *Varroa destructor.*

In another embodiment, the molecules of Formula One may be used to control pest of the Order Symphyla. A non-exhaustive list of particular sp. includes, but is not limited to, *Scutigerella immaculata.*

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis,* and *Rotylenchulus reniformis.*

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula One are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formula One is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Table Section

TABLE 1

Compound Number and Structure

| Compound No. | Appearance | Structure |
|---|---|---|
| 1 | | (structure) |
| 2 | | (structure) |
| 3 | Orange Oil | (structure) |
| 4 | | (structure) |
| 5 | Semi-solid | (structure) |
| 6 | Yellow Oil | (structure) |

TABLE 1-continued

Compound Number and Structure

| Compound No. | Appearance | Structure |
|---|---|---|
| 7 | Yellow Oil | (structure) |
| 8 | Yellow Solid | (structure) |
| 9 | Yellow Oil | (structure) |
| 10 | Yellow Oil | (structure) |
| 11 | Yellow Oil | (structure) |
| 12 | Yellow Oil | (structure) |

TABLE 1-continued

Compound Number and Structure

| Compound No. | Appearance | Structure |
|---|---|---|
| 13 | Yellow Solid | 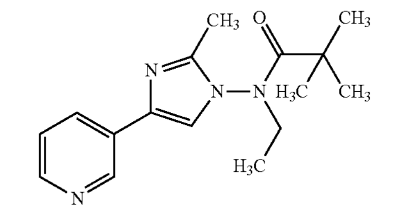 [SMILES: CCN(C(=O)C(C)(C)C)n1cc(-c2cccnc2)nc1C] |
| 14 | Yellow Solid | 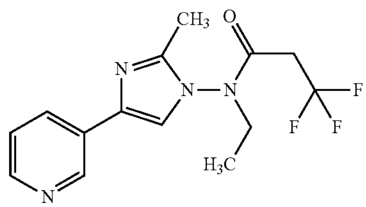 [SMILES: CCN(C(=O)CC(F)(F)F)n1cc(-c2cccnc2)nc1C] |
| 15 | Yellow Oil | 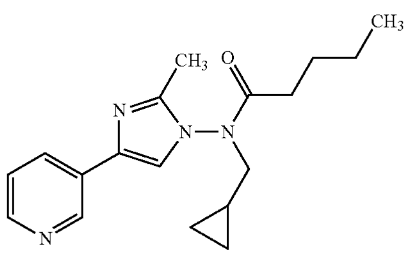 [SMILES: CCCCC(=O)N(CC1CC1)n1cc(-c2cccnc2)nc1C] |
| 16 | Yellow Oil | 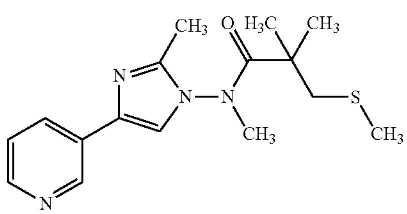 [SMILES: CSCC(C)(C)C(=O)N(C)n1cc(-c2cccnc2)nc1C] |
| 17 | Yellow Oil | 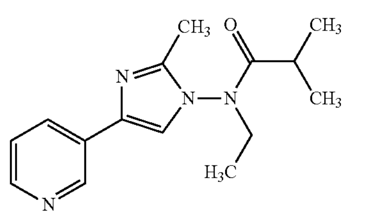 [SMILES: CCN(C(=O)C(C)C)n1cc(-c2cccnc2)nc1C] |
| 18 | Yellow Oil | 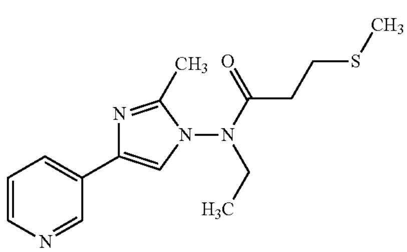 [SMILES: CCN(C(=O)CCSC)n1cc(-c2cccnc2)nc1C] |
| 19 | Yellow Oil | |
| 20 | Yellow Oil | |
| 21 | Yellow Oil | |
| 22 | Yellow Oil | |
| 23 | Yellow Oil | |
| 24 | Yellow Oil | |

TABLE 1-continued

Compound Number and Structure

| Compound No. | Appearance | Structure |
|---|---|---|
| 25 | White Oil | 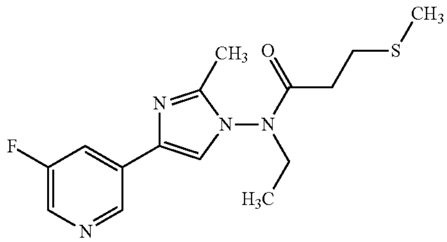 [SMILES: CCN(C(=O)CCSC)n1cc(-c2cncc(F)c2)nc1C] |
| 26 | Yellow Oil | 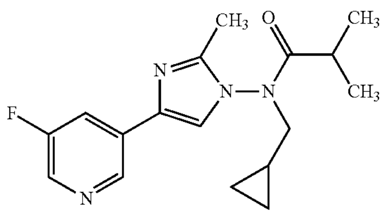 [SMILES: Cc1nc(-c2cncc(F)c2)cn1N(CC1CC1)C(=O)C(C)C] |
| 27 | White Oil | 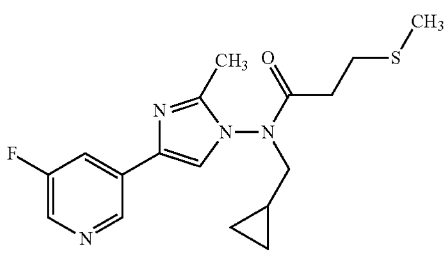 [SMILES: CSCCC(=O)N(CC1CC1)n1cc(-c2cncc(F)c2)nc1C] |
| 28 | Yellow Oil | 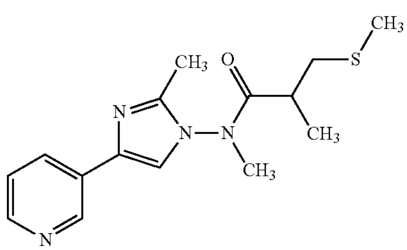 [SMILES: CSCC(C)C(=O)N(C)n1cc(-c2cccnc2)nc1C] |
| 29 | Yellow Oil | 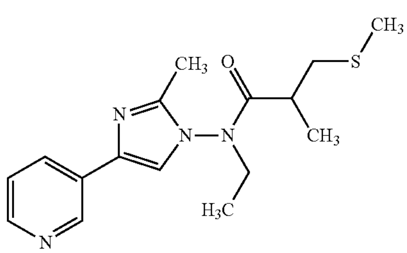 [SMILES: CCN(C(=O)C(C)CSC)n1cc(-c2cccnc2)nc1C] |
| 30 | Yellow Oil | 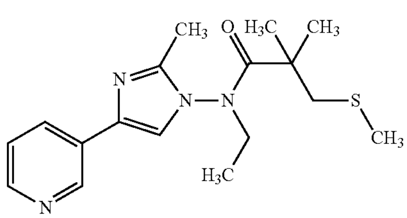 [SMILES: CCN(C(=O)C(C)(C)CSC)n1cc(-c2cccnc2)nc1C] |
| 31 | Yellow Oil | |
| 32 | Yellow Oil | |
| 33 | White Oil | |
| 34 | White Oil | |
| 35 | Yellow Oil | |
| 36 | Yellow Oil | |

TABLE 1-continued

Compound Number and Structure

| Compound No. | Appearance | Structure |
|---|---|---|
| 37 | White Oil | 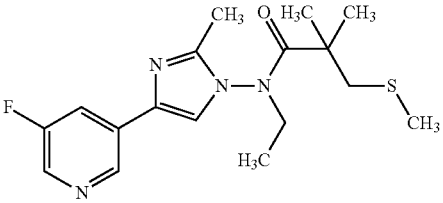 [SMILES: CCN(C(=O)C(C)(C)CSC)n1cc(-c2cncc(F)c2)nc1C] |
| 38 | Yellow Oil | 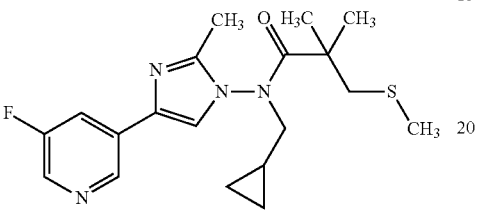 |
| 39 | Brown Solid | 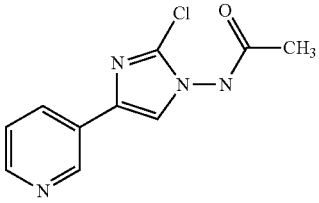 [SMILES: CC(=O)Nn1cc(-c2cccnc2)nc1Cl] |
| 40 | Yellow Oil | 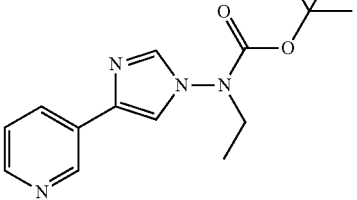 |
| 41 | Yellow Oil | 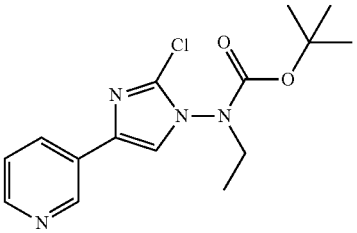 [SMILES: CCN(C(=O)OC(C)(C)C)n1cc(-c2cccnc2)nc1Cl] |

TABLE 2

| Compound No. | MP (° C.) | IR (cm⁻¹) | Mass | HNMR | CNMR |
|---|---|---|---|---|---|
| 1 | 122-125 | | ESIMS m/z 259 (M + 1) | ¹H NMR (400 MHz, DMSO-d₆) δ 8.97 (br s, 1H), 8.42 (dd, J = 4.8, 1.5 Hz, 1H), 8.12-8.01 (m, 2H), 7.41-7.38 (m, 1H), 3.27 (s, 3H), 2.24 (s, 3H), 2.19-2.09 (m, 1H), 0.98 (d, J = 7.2 Hz, 6H). | |
| 2 | | 1682 | ESIMS m/z 304 (M + 1) | ¹H NMR (400 MHz, CDCl₃) δ 8.94 (br s, 1H), 8.47 (dd, J = 5.0, 1.4 Hz, 1H), 8.04 (dt, J = 8.2, 1.5 Hz, 1H), 7.36-7.27 (m, 2H) 3.39 (s, 3H), 3.25-3.18 (m, 1H), 2.38 (s, 3H), 2.27-2.19 (m, 2H), 2.02 (s, 3H), 1.24 (d, J = 6.2 Hz, 3H). | |
| 3 | | 1717 | ESIMS m/z 289 (M + 1) | ¹H NMR (400 MHz, CDCl₃) δ 8.92 (d, J = 2.4 Hz, 1H), 8.43 (dd, J = 4.9, 1.4 Hz, 1H), 8.03 (dt, J = 8.3, 1.6 Hz, 1H), 7.28 (dd, J = 7.7, 4.8 Hz, 1H), 7.21 (s, 1H), 3.38 (s, 3H), 2.36 (s, 3H), 1.43 (s, 9H). | |
| 4 | | 3389, 2978, 2930, 1730, 1478, 1275, 1252, 1156, | ESIMS m/z 289 (M + 1), 287 (M − 1) | ¹H NMR (300 MHz, DMSO, Major isomer) δ 10.41 (s, 1H), 8.81 (s, 1H), 8.39 (s, 1H), 7.95 (d, J = 8.0 Hz, 1H), 7.44-7.28 (m, 1H), 2.21 (s, 3H), 2.18 (s, 3H), 1.46 (s, 9H). | |

TABLE 2-continued

Analytical Data

| Compound No. | MP (° C.) | IR (cm⁻¹) | Mass | HNMR | CNMR |
|---|---|---|---|---|---|
| | | 1017, 951, 711, 573 | | | |
| 5 | | | ESIMS m/z 217 [(M + H)]⁺. | $^1$H NMR (300 MHz, CDCl$_3$) δ 10.87 (s, 1H), 8.76 (s, 1H), 8.36 (br s, 1H), 7.96 (d, J = 7.7, 1H), 7.31-7.20 (m, 2H), 2.25 (s, 3H), 2.13 (s, 3H). | $^{13}$C NMR (76 MHz, CDCl$_3$) δ 169.11, 147.16, 146.66, 145.81, 135.00, 132.92, 124.15, 116.96, 30.11, 21.26, 12.22. |
| 6 | | | ESIMS m/z 231 ([M + H]⁺). | $^1$H NMR (300 MHz, CDCl$_3$) δ 8.98-8.87 (m, 1H), 8.50 (s, 1H), 8.07 (dd, J = 7.6, 2.0 Hz, 1H), 7.36-7.31 (m, 1H), 7.30-7.28 (m, 1H), 3.35 (s, 3H), 2.38 (d, J = 1.3 Hz, 3H), 1.84 (s, 3H). | $^{13}$C NMR (76 MHz, CDCl$_3$) δ 171.74, 148.65, 146.34, 145.35, 137.32, 132.34, 129.32, 123.94, 114.61, 36.83, 20.20, 12.15. |
| 7 | | | ESIMS m/z 273 ([M + H]⁺). | $^1$H NMR (300 MHz, CDCl$_3$) δ 8.93 (s, 1H), 8.47 (s, 1H), 8.11-8.02 (m, 1H), 7.30 (d, J = 1.4 Hz, 2H), 3.31 (d, J = 2.1 Hz, 3H), 2.37 (d, J = 2.1 Hz, 3H), 1.13 (d, J = 2.1 Hz, 9H). | $^{13}$C NMR (76 MHz, CDCl$_3$) δ 153.30, 148.16, 146.33, 136.37, 132.44, 123.63, 116.04, 40.57, 28.44, 27.49, 16.33, 12.63, 12.61. |
| 8 | 130.9-131.5 | | ESIMS m/z 299 ([M + H]⁺). | $^1$H NMR (300 MHz, CDCl$_3$) δ 8.96 (s, 1H), 8.54 (d, J = 4.3 Hz, 1H), 8.08 (d, J = 7.9 Hz, 1H), 7.39-7.31 (m, 1H), 7.30 (s, 1H), 3.43 (s, 3H), 3.05-2.78 (m, 2H), 2.41 (s, 3H). | |
| 9 | | | ESIMS m/z 273 ([M + H]⁺). | $^1$H NMR (300 MHz, CDCl$_3$) δ 8.95 (s, 1H), 8.51 (s, 1H), 8.08 (d, J = 7.9 Hz, 1H), 7.33 (dd, J = 7.6, 5.0 Hz, 1H), 7.26 (s, 1H), 3.38 (s, 3H), 2.37 (s, 3H), 2.12-1.92 (m, 2H), 1.60 (dt, J = 14.8, 7.3 Hz, 2H), 1.35-1.20 (m, 2H), 0.86 (t, J = 7.2 Hz, 3H). | $^{13}$C NMR (76 MHz, CDCl$_3$) δ 174.17, 147.97, 146.43, 145.42, 136.73, 132.21, 123.65, 114.79, 37.11, 31.51, 30.09, 26.99, 22.56, 14.33, 12.43. |
| 10 | | | ESIMS m/z 291 ([M + H]⁺). | $^1$H NMR (300 MHz, CDCl$_3$) δ 8.97-8.89 (d, J = 2.4 Hz, 1H), 8.54-8.44 (m, 1H), 8.11-7.98 (m, 1H), 7.35-7.28 (m, 2H), 3.42-3.38 (s, 3H), 2.85-2.66 (t, J = 6.9 Hz, 2H), 2.42-2.38 (s, 3H), 2.37-2.16 (m, 2H), 2.09-2.00 (s, 3H). | $^{13}$C NMR (76 MHz, CDCl$_3$) δ 172.34, 148.63, 146.47, 145.34, 137.05, 132.21, 128.84, 123.56, 114.79, 37.14, 31.46, 29.22, 16.10, 12.38. |
| 11 | | | ESIMS m/z 313 ([M + H]⁺). | $^1$H NMR (300 MHz, CDCl$_3$) δ 8.92 (s, 1H), 8.47 (s, 1H), 8.08 (d, J = 7.8 Hz, 1H), 7.38-7.23 (m, 2H), 3.81 (dd, J = 14.1, 7.1 Hz, 1H) 3.30 (dd, J = 14.2, 7.1 Hz, 1H), 2.39 (s, 3H), 1.21 (s, 3H), 1.12 (s, 9H), 0.96-0.80 (m, 1H), 0.54-0.43 (m, 2H), 0.08 (d, J = 4.7 Hz, 2H). | $^{13}$C NMR (76 MHz, CDCl$_3$) δ 177.72, 148.07, 147.05, 146.11, 135.23, 132.08, 129.62, 123.72, 117.42, 56.21, 40.51, 29.96, 28.76, 27.70, 12.70, 8.86, 4.34, 3.33. |
| 12 | | | ESIMS m/z 339 ([M + H]⁺). | $^1$H NMR (300 MHz, CDCl$_3$) δ 8.96 (s, 1H), 8.52 (s, 1H), 8.10 (dd, J = 8.0, 1.9 Hz, 1H), 7.36 (dd, J = 8.4, 5.2 Hz, 1H), 7.31 (s, 1H), 3.86-3.71 (m, 1H), 3.66-3.52 (m, 1H), 3.05-2.79 (m, 2H), 2.43 (s, 3H), 0.89 (ddd, J = 7.6, 4.9, 2.7 Hz, 1H), 0.63-0.52 (m, | $^{13}$C NMR (76 MHz, CDCl$_3$) δ 164.22, 148.46, 146.04, 137.03, 132.33, 129.01, 125.67, 123.65, 122.27, 115.77, 53.92, 37.26, 36.87, 36.47, 36.07, 12.21, 8.56, 4.20, 3.44. |

TABLE 2-continued

Analytical Data

| Compound No. | MP (° C.) | IR (cm⁻¹) | Mass | HNMR | CNMR |
|---|---|---|---|---|---|
| | | | | 2H), 0.22 (t, J = 3.8 Hz, 2H). | |
| 13 | | | ESIMS m/z 287 ([M + H]⁺). | $^1$H NMR (300 MHz, CDCl$_3$) δ 8.95 (s, 1H), 8.51 (s, 1H), 8.09 (dt, J = 8.0, 1.8 Hz, 1H), 7.32 (m, 1H), 7.27 (s, 1H), 4.14 (dq, J = 14.3, 7.2 Hz, 1H), 3.40 (dq, J = 14.1, 7.1 Hz, 1H), 2.39 (s, 3H), 1.26-1.17 (m, 3H), 1.14 (s, 9H). | $^{13}$C NMR (76 MHz, CDCl$_3$) δ 177.89, 148.35, 146.90, 135.90, 132.36, 129.57, 123.88, 117.53, 47.56, 40.55, 29.93, 28.66, 27.64, 12.88. |
| 14 | | | ESIMS m/z 313 ([M + H]⁺). | $^1$H NMR (300 MHz, CDCl$_3$) δ 8.98 (d, J = 2.2 Hz, 1H), 8.52 (s, 1H), 8.17-7.99 (m, 1H), 7.43-7.29 (m, 1H), 4.13 (dq, J = 14.4, 7.3 Hz, 1H), 3.68 (dq, J = 14.2, 7.1 Hz, 1H), 2.85 (dt, J = 17.6, 8.2 Hz, 2H), 2.40 (s, 3H), 1.20 (t, J = 7.2 Hz, 3H). | $^{13}$C NMR (76 MHz, CDCl$_3$) δ 148.88, 146.66, 146.01, 132.54, 129.05, 125.45, 123.94, 121.78, 115.69, 44.82, 37.08, 36.61, 29.96, 12.59, 12.19. |
| 15 | | | ESIMS m/z 313 ([M + H]⁺). | $^1$H NMR (300 MHz, CDCl$_3$) δ 8.95 (s, 1H), 8.50 (d, J = 4.8 Hz, 1H), 8.09 (d, J = 7.9 Hz, 1H), 7.33 (dd, J = 8.0, 4.9 Hz, 1H), 7.27-7.26 (m, 2H), 3.82-3.65 (m, 1H), 3.65-3.51 (m, 1H), 2.40 (s, 3H), 2.08-1.92 (m, 2H), 1.59 (p, J = 7.4 Hz, 2H), 1.34-1.15 (m, 4H), 1.01-0.91 (m, 1H), 0.85 (t, J = 7.3 Hz, 3H), 0.54 (d, J = 8.0 Hz, 2H), 0.18 (t, J = 4.6 Hz, 2H). | $^{13}$C NMR (76 MHz, CDCl$_3$) δ 154.33, 153.77, 148.52, 146.65, 132.25, 123.85, 115.84, 53.59, 31.69, 29.94, 26.85, 24.05, 22.55, 14.06, 12.42, 9.17, 4.24, 3.70. |
| 16 | | | ESIMS m/z 319 ([M + H]⁺). | $^1$H NMR (301 MHz, CDCl$_3$) δ 8.98 (s, 1H), 8.51 (s, 1H), 8.21 (d, J = 7.6 Hz, 1H), 7.51-7.34 (m, 2H), 3.36 (s, 3H), 2.84 (d, J = 12.7 Hz, 1H), 2.69-2.58 (m, 1H), 2.45 (s, 3H), 2.15 (s, 3H), 1.24 (s, 3H), 1.15 (d, J = 8.7 Hz, 3H). | $^{13}$C NMR (76 MHz, CDCl$_3$) δ 176.05, 146.89, 146.39, 144.66, 135.66, 133.74, 124.44, 116.68, 47.84, 46.51, 40.76, 30.03, 26.48, 25.90, 18.35, 12.69. |
| 17 | | | ESIMS m/z 273 ([M + H]⁺). | $^1$H NMR (300 MHz, CDCl$_3$) δ 8.93 (s, 1H), 8.48 (s, 1H), 8.06 (d, J = 7.9 Hz, 1H), 7.30 (dd, J = 7.6, 4.8 Hz, 1H), 7.22 (s, 1H), 4.03 (dt, J = 14.3, 7.1 Hz, 1H), 3.61 (dq, J = 14.1, 7.1 Hz, 1H), 2.35 (s, 3H), 2.21 (s, 1H), 1.20-1.15 (m, 3H), 1.08 (d, J = 6.4 Hz, 6H). | $^{13}$C NMR (76 MHz, CDCl$_3$) δ 148.36, 146.47, 146.18, 136.36, 132.27, 123.80, 116.23, 44.53, 30.11, 20.70, 19.54, 12.97, 12.45. |
| 18 | | | ESIMS m/z 305 ([M + H]⁺). | $^1$H NMR (301 MHz, CDCl$_3$) δ 8.92 (s, 1H), 8.47 (s, 1H), 8.06 (d, J = 7.9 Hz, 1H), 7.31 (dd, J = 7.4, 4.1 Hz, 1H), 7.26-7.23 (m, 1H), 4.06 (dq, J = 14.4, 7.1 Hz, 1H), 3.64 (dq, J = 14.3, 7.2 Hz, 1H), 2.75 (t, J = 6.7 Hz, 2H), 2.38 (s, 3H), 2.26 (dd, J = 13.5, 6.7 Hz, 2H), 2.01 (s, 3H), 1.19 (t, J = 7.5 Hz, 3H). | $^{13}$C NMR (76 MHz, CDCl$_3$) δ 171.98, 148.24, 146.28, 146.10, 136.77, 132.45, 129.43, 123.89, 116.06, 44.51, 32.22, 29.39, 16.31, 12.90, 12.49. |
| 19 | | | ESIMS m/z 287 ([M + H]⁺). | $^1$H NMR (300 MHz, CDCl$_3$) δ 8.95 (s, 1H), 8.50 (s, 1H), 8.08 (d, J = 7.8 Hz, 1H), 7.32 (t, J = 6.0 Hz, 1H), 7.21 (s, 1H), 4.05 (dd, J = 13.9, 7.0 Hz, 1H), 3.65 (dd, J = 14.0, 7.0 Hz, 1H), 2.37 (s, 3H), 1.96 (s, 2H), 1.59 (t, J = 7.3 Hz, 2H), | $^{13}$C NMR (76 MHz, CDCl$_3$) δ 148.26, 146.37, 146.12, 132.35, 123.88, 115.97, 44.36, 31.88, 30.03, 26.93, 22.64, 14.16, 12.98, 12.48. |

TABLE 2-continued

Analytical Data

| Compound No. | MP (° C.) | IR (cm$^{-1}$) | Mass | HNMR | CNMR |
|---|---|---|---|---|---|
| | | | | 1.25-1.16 (m, 5H), 0.85 (t, J = 7.2 Hz, 3H). | |
| 20 | | | ESIMS m/z 299 ([M + H]$^+$). | $^1$H NMR (300 MHz, CDCl$_3$) δ 8.92 (s, 1H), 8.47 (s, 1H), 8.05 (d, J = 7.4 Hz, 1H), 7.26 (s, 2H), 3.79-3.61 (m, 1H), 3.55 (dd, J = 14.1, 7.2 Hz, 1H), 2.37 (s, 3H), 2.25 (s, 1H), 1.08 (d, J = 5.9 Hz, 6H), 0.92 (s, 1H), 0.51 (d, J = 7.5 Hz, 2H), 0.14 (d, J = 3.9 Hz, 2H). | $^{13}$C NMR (76 MHz, CDCl$_3$) δ 148.32, 146.47, 136.48, 132.20, 129.47, 123.78, 116.11, 53.77, 30.00, 20.76, 19.52, 12.49, 9.25, 4.38, 3.73. |
| 21 | | | ESIMS m/z 331 ([M + H]$^+$). | $^1$H NMR (300 MHz, CDCl$_3$) δ 8.95 (s, 1H), 8.50 (s, 1H), 8.09 (d, J = 7.9 Hz, 1H), 7.30 (s, 2H), 3.82-3.67 (m, 2H), 3.67-3.53 (m, 1H), 2.78 (t, J = 6.9 Hz, 2H), 2.42 (s, 3H), 2.31 (t, J = 6.8 Hz, 2H), 2.04 (s, 3H), 0.95 (dd, J = 9.8, 5.2 Hz, 1H), 0.55 (d, J = 7.8 Hz, 2H), 0.19 (t, J = 3.9 Hz, 2H). | $^{13}$C NMR (76 MHz, CDCl$_3$) δ 172.12, 148.48, 146.53, 146.29, 136.78, 132.21, 129.33, 123.67, 115.82, 53.83, 32.19, 29.41, 16.32, 12.56, 9.23, 4.44, 3.89. |
| 22 | | | ESIMS m/z 277 ([M + H]$^+$). | $^1$H NMR (300 MHz, CDCl$_3$) δ 8.73 (s, 1H), 8.34 (d, J = 2.3 Hz, 1H), 7.82 (ddd, J = 9.6, 2.7, 1.7 Hz, 1H), 7.30 (s, 1H), 3.38 (s, 3H), 2.37 (s, 3H), 2.17-1.94 (m, 1H), 1.10 (d, J = 6.5 Hz, 6H). | $^{13}$C NMR (76 MHz, CDCl$_3$) δ 146.17, 142.30, 136.75, 136.43, 119.19, 118.93, 115.93, 37.40, 29.77, 29.60, 20.49, 19.41, 12.06. |
| 23 | | | ESIMS m/z 309 ([M + H]$^+$). | $^1$H NMR (300 MHz, CDCl$_3$) δ 8.74 (s, 1H), 8.35 (s, 1H), 7.81 (d, J = 9.3 Hz, 1H), 7.32 (s, 1H), 3.39 (s, 3H), 2.77 (t, J = 6.8 Hz, 2H), 2.39 (s, 3H), 2.30 (dt, J = 13.9, 6.8 Hz, 2H), 2.03 (s, 3H). | $^{13}$C NMR (76 MHz, CDCl$_3$) δ 161.87, 158.47, 145.96, 142.37, 136.90, 136.58, 119.19, 118.94, 115.66, 37.25, 31.88, 29.30, 16.21, 12.13. |
| 24 | | | ESIMS m/z 291 ([M + H]$^+$). | $^1$H NMR (300 MHz, CDCl$_3$) δ 8.75 (s, 1H), 8.36 (s, 1H), 7.83 (d, J = 9.3 Hz, 1H), 7.26 (s, 1H), 4.06 (dq, J = 14.1, 7.1 Hz, 2H), 3.63 (dq, J = 14.2, 7.2 Hz, 2H), 2.37 (s, 3H), 2.29-2.14 (m, 1H), 1.20 (t, J = 7.2 Hz, 3H), 1.10 (d, J = 6.4 Hz, 6H). | $^{13}$C NMR (76 MHz, CDCl$_3$) δ 177.82, 146.53, 142.21, 136.64, 136.33, 119.24, 118.98, 117.05, 44.55, 30.24, 30.10, 20.76, 19.60, 13.08, 12.50 |
| 25 | | | ESIMS m/z 323 ([M + H]$^+$). | $^1$H NMR (300 MHz, CDCl$_3$) δ 8.73 (s, 1H), 8.35 (s, 1H), 7.82 (d, J = 9.6 Hz, 1H), 7.29 (s, 1H), 4.08 (dq, J = 14.0, 7.0 Hz, 1H), 3.66 (dq, J = 14.1, 7.1 Hz, 1H), 2.76 (t, J = 6.9 Hz, 2H), 2.39 (s, 3H), 2.26 (br s, 2H), 2.03 (s, 3H), 1.20 (t, J = 7.2 Hz, 3H). | $^{13}$C NMR (76 MHz, CDCl$_3$) δ 171.95, 146.41, 142.25, 136.65, 136.45, 119.12, 118.91, 116.81, 44.54, 32.20, 29.46, 16.31, 13.00, 12.58, 7.71. |
| 26 | | | ESIMS m/z 317 ([M + H]$^+$). | $^1$H NMR (300 MHz, CDCl$_3$) δ 8.74 (s, 1H), 8.34 (s, 1H), 7.83 (d, J = 9.4 Hz, 1H), 7.32 (s, 1H), 3.82-3.66 (m, 1H), 3.64-3.48 (m, 1H), 2.39 (s, 3H), 2.26 (br s, 1H), 1.10 (d, J = 6.4 Hz, 6H), 0.92 (tt, J = 13.1, 6.3 Hz, 1H), 0.53 (d, J = 7.7 Hz, 2H), 0.16 (t, J = 4.1 Hz, 2H). | $^{13}$C NMR (76 MHz, CDCl$_3$) δ 170.65, 154.09, 146.75, 142.12, 136.49, 136.20, 135.22, 131.18, 119.25, 118.99, 116.98, 29.99, 20.83, 19.60, 12.54, 9.34, 4.49, 3.81. |
| 27 | | | ESIMS m/z 349 ([M + H]$^+$). | $^1$H NMR (300 MHz, CDCl$_3$) δ 8.74 (s, 1H), 8.36 (d, J = 2.6 Hz, 1H), 7.84 (dt, J = 9.6, 2.4 Hz, 1H), 7.34 (s, 1H), 3.76 (dd, J = | $^{13}$C NMR (76 MHz, CDCl$_3$) δ 171.95, 161.77, 158.29, 146.73, 142.14, 136.60, 136.30, |

TABLE 2-continued

Analytical Data

| Compound No. | MP (° C.) | IR (cm⁻¹) | Mass | HNMR | CNMR |
|---|---|---|---|---|---|
| | | | | 14.4, 7.4 Hz, 1H), 3.65-3.53 (m, 1H), 2.78 (t, J = 6.9 Hz, 2H), 2.42 (s, 3H), 2.37-2.23 (m, 2H), 2.05 (s, 3H), 1.03-0.88 (m, 1H), 0.55 (d, J = 7.4 Hz, 2H), 0.18 (t, J = 3.9 Hz, 2H). | 131.17, 119.27, 119.01, 116.71, 53.82, 32.28, 30.11, 29.47, 16.44, 12.58, 9.29, 4.53, 3.89. |
| 28 | | | ESIMS m/z 305 ([M + H]⁺). | ¹H NMR (300 MHz, CDCl₃) δ 8.97 (s, 1H), 8.52 (s, 1H), 8.11 (t, J = 7.1 Hz, 1H), 7.48 (s, 0.5H), 7.36 (s, 1H), 7.29 (s, 0.5H), 3.42 (s, 3H), 2.95-2.80 (m, 1H), 2.54-2.43 (m, 2H), 2.41 (s, 3H), 2.00 (d, J = 13.3 Hz, 3H), 1.16 (t, J = 7.2 Hz, 3H). | ¹³C NMR (76 MHz, CDCl₃) δ 176.76, 148.16, 146.21, 132.54, 116.13, 115.28, 39.07, 38.18, 37.55, 36.55, 35.41, 19.62, 18.68, 16.90, 12.32. |
| 29 | | | ESIMS m/z 319 ([M + H]⁺). | ¹H NMR (300 MHz, CDCl₃) δ 8.91 (s, 1H), 8.45 (d, J = 4.5 Hz, 1H), 8.12-7.99 (m, 1H), 7.42 (s, 0.5H), 7.30 (d, J = 5.6 Hz, 1H), 7.26 (s, 0.5H), 4.11 (dd, J = 13.8, 6.9 Hz, 1H), 3.57 (dq, J = 13.8, 6.9 Hz, 1H), 2.95-2.73 (m, 1H), 2.55-2.42 (m, 2H), 2.36 (s, 3H), 1.95 (d, J = 14.8 Hz, 3H), 1.30-1.01 (m, 6H). | ¹³C NMR (76 MHz, CDCl₃) δ 176.42, 148.08, 146.08, 132.32, 123.96, 117.37, 116.50, 44.77, 40.20, 39.12, 38.11, 35.56, 18.63, 16.84, 12.95, 12.45. |
| 30 | | | ESIMS m/z 333 ([M + H]⁺). | ¹H NMR (301 MHz, CDCl₃) δ 8.92 (s, 1H), 8.46 (d, J = 4.1 Hz, 1H), 8.05 (d, J = 7.9 Hz, 1H), 7.37 (s, 1H), 7.32-7.27 (m, 1H), 4.13 (dq, J = 14.3, 7.2 Hz, 1H), 3.39 (d, J = 14.1, 7.1 Hz, 1H), 2.81 (d, J = 12.6 Hz, 1H), 2.58 (d, J = 12.6 Hz, 1H), 2.42 (s, 3H), 2.12 (s, 3H), 1.17 (t, J = 7.2 Hz, 3H), 1.09 (d, J = 6.8 Hz, 6H). | ¹³C NMR (76 MHz, CDCl₃) δ 175.70, 148.33, 146.93, 146.46, 136.00, 132.29, 123.83, 117.50, 48.08, 47.85, 46.66, 30.08, 26.45, 25.95, 18.42, 13.04, 12.70. |
| 31 | | | ESIMS m/z 245 ([M + H]⁺). | ¹H NMR (300 MHz, CDCl₃) δ 8.98 (s, 1H), 8.52 (s, 1H), 8.11 (d, J = 7.3 Hz, 1H), 7.33 (d, J = 7.7 Hz, 1H), 7.30 (s, 1H), 4.04 (t, J = 6.5 Hz, 1H), 3.68 (dd, J = 13.5, 6.6 Hz, 1H), 2.40 (s, 3H), 1.87 (s, 3H), 1.23 (d, J = 6.2 Hz, 3H). | ¹³C NMR (76 MHz, CDCl₃) δ 172.33, 171.04, 148.26, 146.35, 145.86, 132.37, 123.82, 115.86, 44.22, 20.66, 12.96, 12.46, 7.78. |
| 32 | | | ESIMS m/z 359 ([M + H]⁺). | ¹H NMR (301 MHz, CDCl₃) δ 8.91 (s, 1H), 8.44 (s, 1H), 8.05 (dt, J = 7.9, 1.8 Hz, 1H), 7.41 (s, 1H), 7.32-7.24 (m, 1H), 3.84 (dd, J = 14.1, 7.2 Hz, 1H), 3.33 (dd, J = 14.1, 7.2 Hz, 1H), 2.81 (d, J = 12.7 Hz, 1H), 2.57 (d, J = 12.6 Hz, 1H), 2.43 (s, 3H), 2.11 (s, 3H), 1.10 (d, J = 8.5 Hz, 6H), 0.89 (dtd, J = 12.1, 7.4, 2.6 Hz, 1H), 0.48 (ddd, J = 7.7, 4.1, 2.6 Hz, 2H), 0.10 (dt, J = 6.5, 3.1 Hz, 2H). | ¹³C NMR (76 MHz, CDCl₃) δ 175.95, 172.32, 148.33, 147.19, 146.48, 135.89, 132.21, 123.82, 117.54, 56.75, 48.14, 46.84, 26.53, 25.98, 18.43, 13.15, 8.98, 4.64, 3.78. |
| 33 | | | ESIMS m/z 271 ([M + H]⁺). | ¹H NMR (300 MHz, CDCl₃) δ 8.97 (s, 1H), 8.52 (s, 1H), 8.10 (d, J = 7.9 Hz, 1H), 7.34-7.32 (m, 1H), 7.31 (s, 1H), 3.85-3.67 (m, 1H), 3.67-3.54 (m, 1H), 2.43 (s, 3H), 1.89 (s, | ¹³C NMR (76 MHz, CDCl₃) δ 171.14, 148.35, 146.48, 146.24, 136.66, 132.28, 123.77, 115.45, 53.57, 20.63, 12.57, 9.77, 9.33, |

TABLE 2-continued

Analytical Data

| Compound No. | MP (° C.) | IR (cm⁻¹) | Mass | HNMR | CNMR |
|---|---|---|---|---|---|
| | | | | 3H), 0.96 (ddd, J = 12.4, 7.7, 4.8 Hz, 1H), 0.56 (d, J = 7.8 Hz, 2H), 0.20 (t, J = 4.6 Hz, 2H). | 4.45, 3.94. |
| 34 | | | ESIMS m/z 323 ([M + H]⁺). | ¹H NMR (300 MHz, CDCl₃) δ 8.75 (s, 1H), 8.37 (s, 1H), 7.91-7.75 (m, 1H), 7.52 (s, 0.5H), 7.32 (s, 0.5H), 3.42 (s, 3H), 2.99-2.79 (m, 1H), 2.55-2.44 (m, 2H), 2.42 (s, 3H), 2.02 (d, J = 12.8 Hz, 3H), 1.17 (t, J = 6.7 Hz, 3H). | ¹³C NMR (76 MHz, CDCl₃) δ 176.70, 145.86, 142.09, 136.74, 119.18, 116.83, 115.94, 39.07, 38.17, 37.62, 36.60, 35.47, 32.32, 23.11, 18.71, 16.87, 12.27. |
| 35 | | | ESIMS m/z 337 ([M + H]⁺). | ¹H NMR (301 MHz, CDCl₃) δ 8.74 (s, 1H), 8.35 (d, J = 2.1 Hz, 1H), 7.83 (dt, J = 9.6, 2.2 Hz, 1H), 7.45 (s, 1H), 3.36 (s, 3H), 2.83-2.77 (m, 1H), 2.69-2.60 (m, 1H), 2.46 (s, 3H), 2.16 (s, 3H), 1.16 (d, J = 7.4 Hz, 6H). | ¹³C NMR (76 MHz, CDCl₃) δ 176.01, 146.99, 142.17, 136.61, 136.30, 119.27, 119.01, 116.89, 47.91, 46.59, 45.63, 40.80, 30.10, 26.52, 25.98, 25.23, 18.42, 12.73. |
| 36 | | | ESIMS m/z 337 ([M + H]⁺). | ¹H NMR (300 MHz, CDCl₃) δ 8.74 (s, 1H), 8.33 (s, 1H), 7.80 (d, J = 8.5 Hz, 1H), 7.47 (s, 0.5H), 7.28 (s, 0.5H), 4.21-3.98 (m, 1H), 3.57 (dd, J = 13.3, 6.7 Hz, 1H), 2.85 (dq, J = 23.7, 13.2, 11.6 Hz, 1H), 2.47-2.43 (m, 2H), 2.37 (s, 3H), 1.96 (d, J = 14.0 Hz, 3H), 1.24-1.01 (m, 6H). | ¹³C NMR (76 MHz, CDCl₃) δ 176.30, 146.93, 146.29, 141.89, 136.15, 135.01, 118.99, 118.14, 117.23, 44.78, 39.11, 38.08, 36.83, 35.63, 18.66, 16.84, 12.84, 12.40. |
| 37 | | | ESIMS m/z 351 ([M + H]⁺). | ¹H NMR (300 MHz, CDCl₃) δ 8.77 (s, 1H), 8.36 (s, 1H), 7.85 (d, J = 9.5 Hz, 1H), 7.43 (s, 1H), 4.16 (dq, J = 14.3, 7.2 Hz, 1H), 3.44 (dq, J = 14.1, 7.1 Hz, 1H), 2.83 (d, J = 12.7 Hz, 1H), 2.62 (d, J = 12.7 Hz, 1H), 2.45 (s, 3H), 2.16 (s, 3H), 1.20 (t, J = 7.2 Hz, 3H), 1.14 (d, J = 2.7 Hz, 6H). | ¹³C NMR (76 MHz, CDCl₃) δ 175.61, 147.23, 142.17, 136.65, 136.23, 134.79, 119.21, 118.84, 118.27, 48.07, 47.85, 46.68, 26.41, 26.06, 18.44, 13.01, 12.73. |
| 38 | | | ESIMS m/z 377 ([M + H]⁺). | ¹H NMR (300 MHz, CDCl₃) δ 8.77 (s, 1H), 8.36 (s, 1H), 7.91-7.74 (m, 1H), 7.49 (s, 1H), 3.89 (dd, J = 14.1, 7.2 Hz, 1H), 3.38 (dd, J = 14.2, 7.2 Hz, 1H), 2.90-2.80 (m, 1H), 2.68-2.58 (m, 1H), 2.47 (s, 3H), 2.16 (s, 3H), 1.15 (d, J = 4.7 Hz, 6H), 0.93 (tdd, J = 12.2, 6.1, 2.6 Hz, 1H), 0.53 (dd, J = 7.8, 3.5 Hz, 2H), 0.14 (dd, J = 7.9, 3.7 Hz, 2H). | ¹³C NMR (76 MHz, CDCl₃) δ 175.83, 147.51, 142.19, 136.50, 136.19, 134.60, 119.13, 118.94, 118.23, 56.80, 48.07, 46.86, 26.50, 26.06, 18.45, 13.11, 8.98, 4.65, 3.78. |
| 39 | 129-39 | | ESIMS m/z 237 ([M + H]⁺). | ¹H NMR (300 MHz, CDCl₃) δ 10.68 (s, 1H), 8.80 (s, 1H), 8.43 (s, 1H), 8.01 (d, J = 7.5 Hz, 1H), 7.33 (s, 2H), 2.20 (s, 3H). | |
| 40 | | | ESIMS m/z 289 ([M + H]⁺). | ¹H NMR (400 MHz, CD₃CN) δ 9.00 (d, J = 2.5 Hz, 1H), 8.46 (d, J = 4.8 Hz, 1H), 8.11 (m, 1H), 7.67 (d, J = 1.3 Hz, 1H), 7.61 (d, J = 1.2 Hz, 1H), 7.36 (m, 1H), 3.76 (q, J = 7.1 Hz, 2H), 1.45 (s, 9H), 1.17 (t, J = 7.2 Hz, 3H). | |
| 41 | | | ESIMS m/z 323 ([M + H]⁺). | ¹H NMR (600 MHz, CDCl₃) δ 8.92 (d, J = 1.6 Hz, 1H), 8.50 (dd, J = 4.8, 1.5 Hz, 1H), 8.06 (dt, J = | ¹³C NMR (151 MHz, CDCl₃) δ 152.90, 148.47, 146.02, 136.07, 134.08, |

TABLE 2-continued

| | | Analytical Data | | | |
|---|---|---|---|---|---|
| Compound No. | MP (° C.) | IR (cm$^{-1}$) | Mass | HNMR | CNMR |
| | | | | 7.9, 2.0 Hz, 1H), 7.33-7.27 (m, 2H), 3.89 (dq, J = 14.5, 7.3 Hz, 1H), 3.68 (dq, J = 14.3, 7.2 Hz, 1H), 1.44 (s, 9H), 1.22 (t, J = 7.2 Hz, 3H). | 131.81, 128.79, 123.36, 117.66, 83.23, 45.32, 28.04, 13.03. |

TABLE 3

MYZUPE and BEMITA Rating Table
GPA and BEMITA Rating Table

| % Control (or Mortality) | Rating |
|---|---|
| 80-100 | A |
| More than 0-Less than 80 | B |
| Not Tested | C |
| No activity noticed in this bioassay | D |

TABLE 4

Biological Data for MYZUPE and BEMITA

| Compound No. | MYZUPE % Ctrl @ 200 ppm | BEMITA % Ctrl @ 200 ppm |
|---|---|---|
| 1 | B | B |
| 2 | B | D |
| 3 | B | B |
| 4 | D | B |
| 5 | A | A |
| 6 | B | A |
| 7 | B | A |
| 8 | B | A |
| 9 | B | A |
| 10 | B | A |
| 11 | B | A |
| 12 | D | A |
| 13 | D | B |
| 14 | D | D |
| 15 | B | A |
| 16 | D | D |
| 17 | B | B |
| 18 | A | A |
| 19 | B | A |
| 20 | B | D |
| 21 | B | A |
| 22 | B | A |
| 23 | A | A |
| 24 | B | B |
| 25 | B | A |
| 26 | B | B |
| 27 | B | A |
| 28 | C | C |
| 29 | C | C |
| 30 | C | C |
| 31 | C | C |
| 32 | C | C |
| 33 | C | C |
| 34 | C | C |
| 35 | C | C |
| 36 | C | C |
| 37 | C | C |
| 38 | C | C |
| 39 | C | C |
| 40 | C | C |
| 41 | B | A |

We claim:

1. A process comprising applying a composition comprising a molecule according to Formula One:

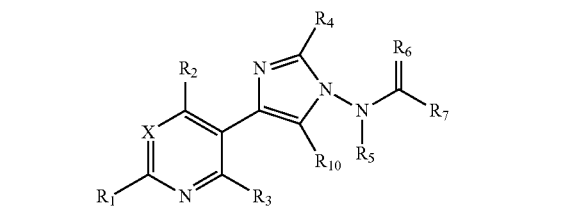

Formula One wherein
(a) X is CR8;
(b) R1 is H;
(c) R2 is H;
(d) R3 is H;
(e) R4 is H, F, Cl, Br, I, or unsubstituted $C_1$-$C_6$ alkyl;
(f) R5 is H, substituted or unsubstituted $C_1$-$C_6$ alkyl wherein said unsubstituted $C_1$-$C_6$ alkyl has a $C_3$-$C_{10}$ cycloalkyl;
(g) R6 is O;
(h) R7 is substituted or unsubstituted $C_1$-$C_6$ alkyl OR9, R9S(O)$_n$R9,
  wherein each said R7, which is substituted, has one or more substituents selected from F, Cl, Br, or I;
(i) R8 is H, F, Cl, Br, or I;
(j) R9 (each independently) is unsubstituted $C_1$-$C_6$ alkyl;
(k) R10 is H or unsubstituted $C_1$-$C_6$ alkyl; and
(l) n is (each independently) 0;
to an area to control a pest, in an amount sufficient to control such pest.

2. A process according to claim 1 wherein said molecule said R4 is F, Cl, or unsubstituted $C_1$-$C_2$ alkyl.

3. A process according to claim 1 wherein said molecule said R4 is Cl or $CH_3$.

4. A process according to claim 1 wherein said molecule said R5 is H, $CH_3$, $CH_2$-cyclopropyl, or $CH_2CH_3$.

5. A process according to claim 1 wherein said molecule said R7 is a substituted $C_1$-$C_6$ alkyl wherein said substituent is one or more F or Cl or a combination thereof.

6. A process according to claim 1 wherein said molecule said R7 is a substituted $C_1$-$C_6$ alkyl wherein said substituent is one or more F.

7. A process according to claim 1 wherein said molecule said R7 is $CH_2CF_3$.

8. A process according to claim 1 wherein said molecule said R7 is a unsubstituted $C_1$-$C_6$ alkyl.

9. A process according to claim 1 wherein said molecule said R7 is $CH(CH_3)_2$, $CH_3$, $C(CH_3)_3$, or $CH_2CH_2CH_3$.

10. A process according to claim 1 wherein said molecule said R7 is OR9.

11. A process according to claim 1 wherein said molecule said R7 is O(unsubstituted $C_1$-$C_6$ alkyl).

12. A process according to claim 1 wherein said molecule said R7 is $OC(CH_3)_3$.

13. A process according to claim 1 wherein said molecule said R7 is $R9S(O)_nR9$.

14. A process according to claim 1 wherein said molecule said R7 is (unsubstituted $C_1$-$C_6$ alkyl)S(unsubstituted $C_1$-$C_6$ alkyl).

15. A process according to claim 1 wherein said molecule said R7 is $CH_2CH(CH_3)SCH_3$, $CH_2CH_2SCH_3$, $CH(CH_3)_2SCH_3$, or $CH(CH_3)CH_2SCH_3$.

16. A process according to claim 1 wherein said molecule said R8 is H, F, or Cl.

17. A process according to claim 1 wherein said molecule said R8 is H or F.

18. A process according to claim 1 wherein said molecule said R10 is H or $CH_3$.

19. A process according to claim 1 wherein said molecule is selected from

| Compound No. | Structure |
|---|---|
| 1 | |
| 2 | |
| 4 | |
| 5 | |
| 6 | 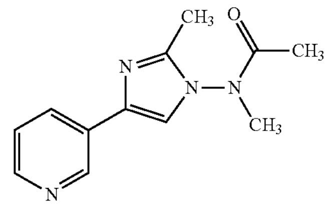 [SMILES: CC(=O)N(C)n1cc(-c2cccnc2)nc1C] |
| 7 | 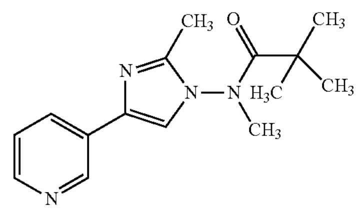 [SMILES: Cc1nc(-c2cccnc2)cn1N(C)C(=O)C(C)(C)C] |
| 8 | 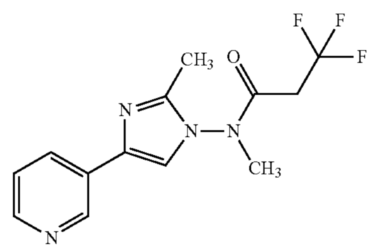 [SMILES: Cc1nc(-c2cccnc2)cn1N(C)C(=O)CC(F)(F)F] |
| 9 | 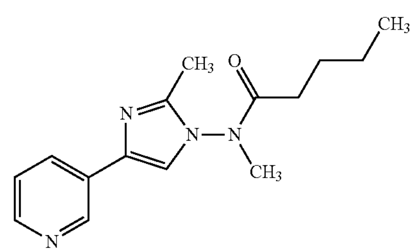 [SMILES: CSCCC(=O)N(C)n1cc(-c2cccnc2)nc1C] |
| 10 | 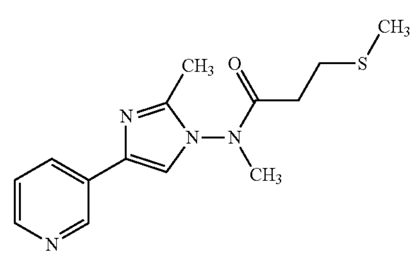 |
| 11 | 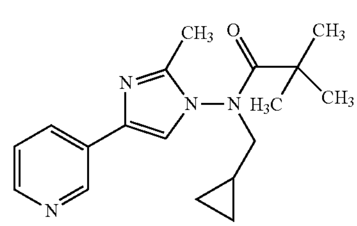 [SMILES: Cc1nc(-c2cccnc2)cn1N(CC1CC1)C(=O)C(C)(C)C] |

| Compound No. | Structure |
|---|---|
| 12 | 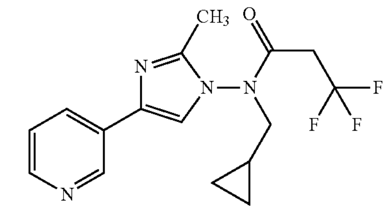 [SMILES: Cc1nc(-c2cccnc2)cn1N(CC1CC1)C(=O)CC(F)(F)F] |
| 13 | 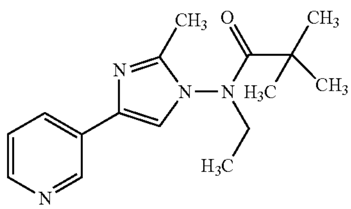 [SMILES: CCN(C(=O)C(C)(C)C)n1cc(-c2cccnc2)nc1C] |
| 15 | 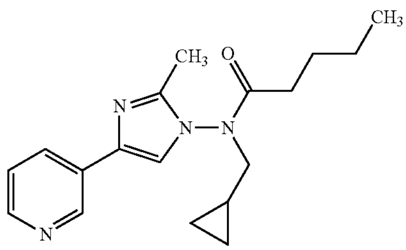 |
| 17 | 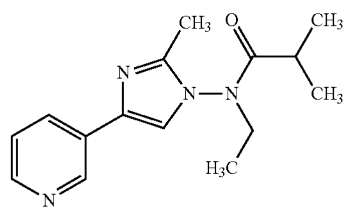 [SMILES: CCN(C(=O)C(C)C)n1cc(-c2cccnc2)nc1C] |
| 18 | 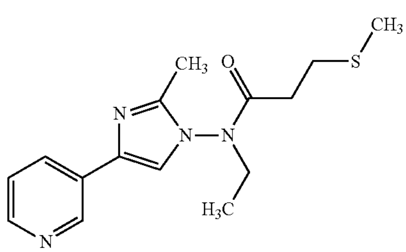 |
| 19 | 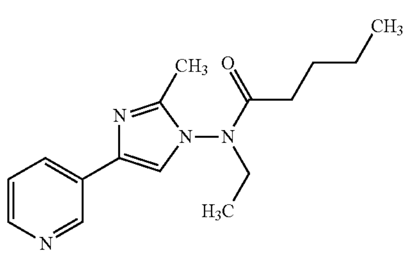 |
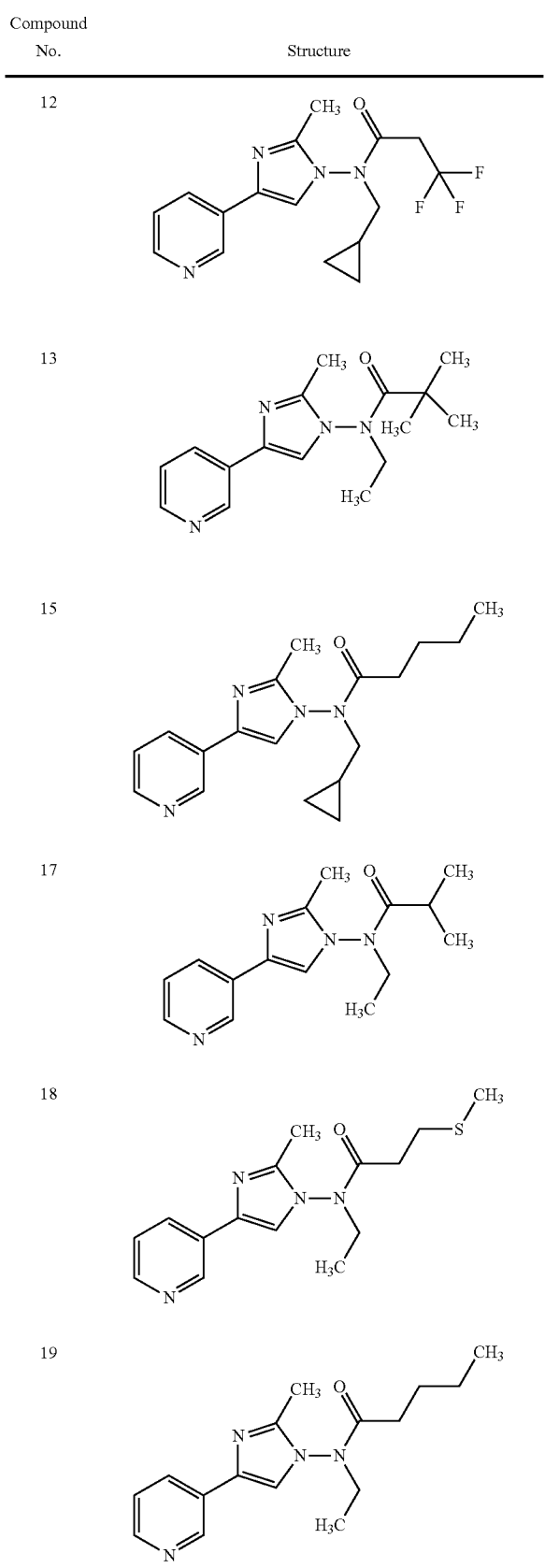
| Compound No. | Structure |
|---|---|
| 20 | 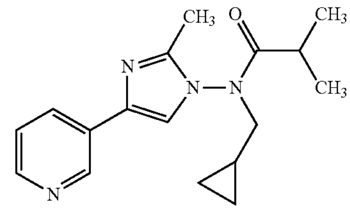 [SMILES: Cc1nc(-c2cccnc2)cn1N(CC1CC1)C(=O)C(C)C] |
| 21 | 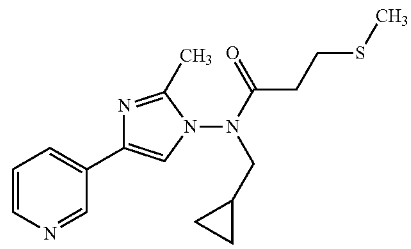 |
| 22 | 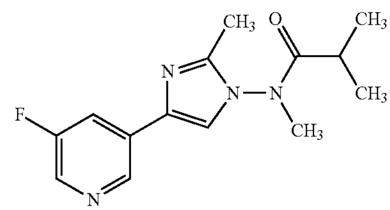 [SMILES: Cc1nc(-c2cncc(F)c2)cn1N(C)C(=O)C(C)C] |
| 23 | 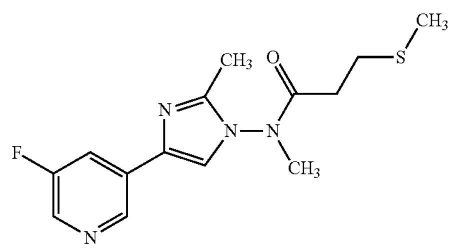 [SMILES: CSCCC(=O)N(C)n1cc(-c2cncc(F)c2)nc1C] |
| 24 | 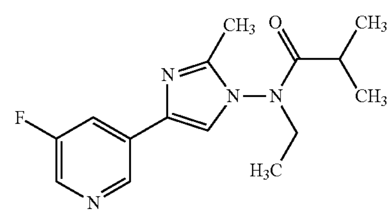 [SMILES: CCN(C(=O)C(C)C)n1cc(-c2cncc(F)c2)nc1C] |
| 25 | 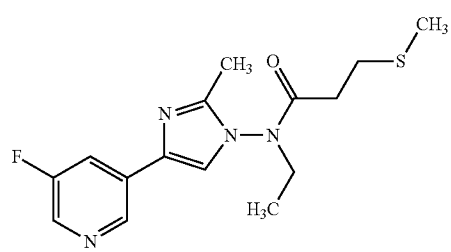 [SMILES: CCN(C(=O)CCSC)n1cc(-c2cncc(F)c2)nc1C] |
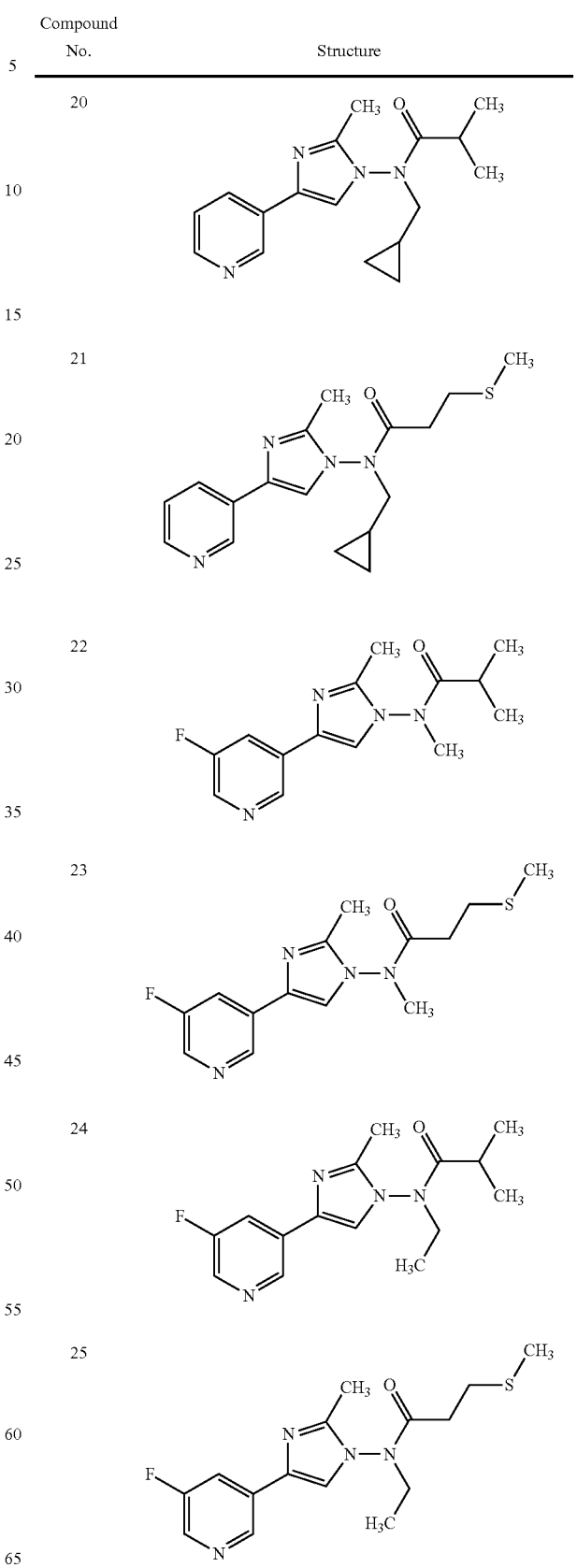

-continued

| Compound No. | Structure |
|---|---|
| 26 | (5-fluoropyridin-3-yl imidazole with N-N-C(O)CH(CH3)2 and N-CH2-cyclopropyl) |
| 27 | (5-fluoropyridin-3-yl imidazole with N-N-C(O)CH2CH2SCH3 and N-CH2-cyclopropyl) |
| 28 | (pyridin-3-yl imidazole with N-N(CH3)-C(O)CH(CH3)CH2SCH3) |
| 29 | (pyridin-3-yl imidazole with N-N(Et)-C(O)CH(CH3)CH2SCH3) |
| 31 | (pyridin-3-yl imidazole with N-N(Et)-C(O)CH3) |
| 33 | (pyridin-3-yl imidazole with N-N(CH2-cyclopropyl)-C(O)CH3) |

-continued

| Compound No. | Structure |
|---|---|
| 34 | (5-fluoropyridin-3-yl imidazole with N-N(CH3)-C(O)CH(CH3)CH2SCH3) |
| 36 | (5-fluoropyridin-3-yl imidazole with N-N(Et)-C(O)CH(CH3)CH2SCH3) |
| 39 | (pyridin-3-yl imidazole with N-NH-C(O)CH3) |
| 40 | (pyridin-3-yl imidazole (no 2-methyl) with N-N(Et)-C(O)O-tBu) |
| 41 | (pyridin-3-yl imidazole with N-N(Et)-C(O)O-tBu) |

20. A process according to claim 1 further comprising:
(a) one or more compounds having acaricidal, algicidal, avicidal, bactericidal, fungicidal, herbicidal, insecticidal, molluscicidal, nematicidal, rodenticidal, or virucidal properties; or
(b) one or more compounds that are antifeedants, bird repellents, chemosterilants, herbicide safeners, insect attractants, insect repellents, mammal repellents, mating disrupters, plant activators, plant growth regulators, or synergists; or
(c) both (a) and (b).

21. A process according to claim 1 wherein further comprising one or more compounds selected from: (3-ethoxypropyl)mercury bromide, 1,2-dichloropropane, 1,3-dichloropropene, 1-methylcyclopropene, 1-naphthol, 2-(octylthio)

ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloramolamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

22. A process according to claim 1 further comprising an agriculturally acceptable carrier.

23. A process according to claim 1 wherein said molecule is in the form of a pesticidally acceptable acid addition salt.

24. A process according to claim 1 wherein said molecule is in the form of a salt derivative.

25. A process according to claim 1 wherein said molecule is in the form a hydrate.

26. A process according to claim 1 wherein said molecule is in the form an ester derivative.

27. A process according to claim 1 wherein said molecule is in the form a crystal polymorph.

28. A process according to claim 1 wherein said molecule has a $^2$H in place of $^1$H.

29. A process according to claim 1 wherein said molecule has a $^{14}C$ in place of a $^{12}C$.

30. A process according to claim 1 further comprising a biopesticide.

31. A process according to claim 1 further comprising one or more of the following compounds:
   (a) 3-(4-chloro-2,6-dimethylphenyl)-4-hydroxy-8-oxa-1-azaspiro[4,5]dec-3-en-2-one;
   (b) 3-(4'-chloro-2,4-dimethyl[1,1'-biphenyl]-3-yl)-4-hydroxy-8-oxa-1-azaspiro[4,5]dec-3-en-2-one;
   (c) 4-[[(6-chloro-3-pyridinyl)methyl]methylamino]-2(5H)-furanone;
   (d) 4-[[(6-chloro-3-pyridinyl)methyl]cyclopropylamino]-2(5H)-furanone;
   (e) 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
   (f) 2-cyano-N-ethyl-4-fluoro-3-methoxy-benenesulfonamide;
   (g) 2-cyano-N-ethyl-3-methoxy-benzenesulfonamide;
   (h) 2-cyano-3-difluoromethoxy-N-ethyl-4-fluoro-benzenesulfonamide;
   (i) 2-cyano-3-fluoromethoxy-N-ethyl-benzenesulfonamide;
   (j) 2-cyano-6-fluoro-3-methoxy-N,N-dimethyl-benzenesulfonamide;
   (k) 2-cyano-N-ethyl-6-fluoro-3-methoxy-N-methyl-benzenesulfonamide;
   (l) 2-cyano-3-difluoromethoxy-N,N-dimethylbenzenesulfon-amide;
   (m) 3-(difluoromethyl)-N-[2-(3,3-dimethylbutyl)phenyl]-1-methyl-1H-pyrazole-4-carboxamide;
   (n) N-ethyl-2,2-dimethylpropionamide-2-(2,6-dichloro-α,α,α-trifluoro-p-tolyl) hydrazone;
   (o) N-ethyl-2,2-dichloro-1-methylcyclopropane-carboxamide-2-(2,6-dichloro-α,α,α-trifluoro-p-tolyl) hydrazone nicotine;
   (p) O-{(E-)-[2-(4-chloro-phenyl)-2-cyano-1-(2-trifluoromethylphenyl)-vinyl]}S-methyl thiocarbonate;
   (q) (E)-N1-[(2-chloro-1,3-thiazol-5-ylmethyl)]-N2-cyano-N1-methylacetamidine;
   (r) 1-(6-chloropyridin-3-ylmethyl)-7-methyl-8-nitro-1,2,3,5,6,7-hexahydro-imidazo[1,2-a]pyridin-5-ol;
   (s) 4-[4-chlorophenyl-(2-butylidine-hydrazono)methyl]phenyl mesylate; and
   (t) N-Ethyl-2,2-dichloro-1-methylcyclopropanecarboxamide-2-(2,6-dichloro-alpha,alpha,alpha-trifluoro-p-tolyl)hydrazone.

32. A process according to claim 1 further comprising a compound having one or more of the following modes of action: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs).

33. A process according to claim 1 further comprising a seed.

34. A process according to claim 1 further comprising a seed that has been genetically modified to express one or more specialized traits.

35. A process according to claim 1 wherein said composition is encapsulated inside, or placed on the surface of, a capsule.

36. A process according to claim 1 wherein said composition is encapsulated inside, or placed on the surface of, a capsule, wherein said capsule has a diameter of about 100-900 nanometers or about 10-900 microns.

37. A process according to claim 1 wherein said pest is selected from beetles, earwigs, cockroaches, flies, aphids, scales, whiteflies, leafhoppers, ants, wasps, termites, moths, butterflies, lice, grasshoppers, locusts, crickets, fleas, *thrips*, bristletails, mites, ticks, nematodes, and symphylans.

38. A process according to claim 1 wherein said pest is from the Phyla Nematoda or Arthropoda.

39. A process according to claim 1 wherein said pest is from the Subphyla Chelicerata, Myriapoda, or Hexapoda.

40. A process according to claim 1 wherein said pest is from the Class of Arachnida, Symphyla, or Insecta.

41. A process according to claim 1 wherein said pest is from the Order Anoplura, Order Coleoptera, Order Dermaptera, Order Blattaria, Order Diptera, Order Hemiptera, Order Hymenoptera, Order Isoptera, Order Lepidoptera, Order Mallophaga, Order Orthoptera, Order Siphonaptera, Order Thysanoptera, Order Thysanura, Order Acarina, or Order Symphyla.

42. A process according to claim 1 wherein said pest is MYZUPE or BEMITA.

43. A process according to claim 1 wherein said amount is from about 0.01 grams per hectare to about 5000 grams per hectare.

44. A process according to claim 1 wherein said amount is from about 0.1 grams per hectare to about 500 grams per hectare.

45. A process according to claim 1 wherein said amount is from about 1 gram per hectare to about 50 grams per hectare.

46. A process according to claim 1 wherein said area is an area where apples, corn, cotton, soybeans, canola, wheat, rice, sorghum, barley, oats, potatoes, oranges, alfalfa, lettuce, strawberries, tomatoes, peppers, crucifers, pears, tobacco, almonds, sugar beets, or beans, are growing, or the seeds thereof are going to be planted.

47. A process according to claim 1 further comprising applying said composition to a genetically modified plant that has been genetically modified to express one or more specialized traits.

48. A process according to claim 1 where said composition further comprises ammonium sulfate.

* * * * *